(12) United States Patent
Mariampillai et al.

(10) Patent No.: US 12,396,803 B2
(45) Date of Patent: *Aug. 26, 2025

(54) SYSTEMS AND METHODS FOR PERFORMING INTRAOPERATIVE GUIDANCE

(71) Applicant: 7D SURGICAL ULC, Toronto (CA)

(72) Inventors: Adrian Mariampillai, Toronto (CA); Victor X. D. Yang, North York (CA); Kenneth Kuei-Ching Lee, North York (CA); Michael K. K. Leung, Markham (CA); Beau Anthony Standish, Toronto (CA)

(73) Assignee: 7D SURGICAL ULC, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/623,674

(22) Filed: Apr. 1, 2024

(65) Prior Publication Data
US 2024/0423723 A1    Dec. 26, 2024

Related U.S. Application Data

(63) Continuation of application No. 17/044,538, filed as application No. PCT/CA2019/050424 on Apr. 8, 2019, now Pat. No. 11,944,390.
(Continued)

(51) Int. Cl.
*A61B 34/20* (2016.01)
*A61B 90/00* (2016.01)

(52) U.S. Cl.
CPC .............. *A61B 34/20* (2016.02); *A61B 90/37* (2016.02); *A61B 90/39* (2016.02);
(Continued)

(58) Field of Classification Search
CPC .. A61B 2034/2046–2074; A61B 34/20; A61B 34/25; A61B 2034/252–258;
(Continued)

(56) References Cited

U.S. PATENT DOCUMENTS 8,864,652 B2    10/2014    Diolaiti et al.
11,197,722 B2    12/2021    Tako et al.
(Continued)

FOREIGN PATENT DOCUMENTS

CN    101904770 A    12/2010
CN    102170835 A    8/2011
(Continued)

*Primary Examiner* — Amelie R Davis
(74) *Attorney, Agent, or Firm* — Stephen Leonard; Aird & McBurney LP

(57) ABSTRACT

Systems and methods are provided in which an intraoperative video feed is augmented with one or more virtual display features based on a detected orientation and position of the tracked medical instrument. In some example embodiments, the virtual display features may be employed to represent, in an augmented video feed, information associated with a previously-detected intraoperative position and orientation of the tracked medical instrument. The virtual display element may be employed, for example, to facilitate the alignment of an untracked medical instrument with a previously determined intraoperative position and orientation of the tracked medical instrument. In other example embodiments, the virtual display element may be dynamically displayed in a fixed spatial relationship relative to the tracked medical instrument.

20 Claims, 17 Drawing Sheets

Related U.S. Application Data

(60) Provisional application No. 62/736,348, filed on Sep. 25, 2018, provisional application No. 62/655,102, filed on Apr. 9, 2018.

(52) U.S. Cl.
CPC . *A61B 2034/2055* (2016.02); *A61B 2090/365* (2016.02); *A61B 2090/3983* (2016.02)

(58) Field of Classification Search
CPC ............ A61B 90/39; A61B 2090/3904; A61B 2090/3916; A61B 2090/3937; A61B 2090/3945; A61B 2090/3941; A61B 2090/3966; A61B 2090/3983; A61B 2090/397; A61B 2090/3975; A61B 2090/3995; A61B 2090/3979; A61B 2090/365; A61B 2090/364
See application file for complete search history.

(56) References Cited

U.S. PATENT DOCUMENTS

2005/0085718 A1  4/2005  Shahidi
2019/0290297 A1  9/2019  Haider et al.

FOREIGN PATENT DOCUMENTS

| | | |
|---|---|---|
| CN | 105358085 A | 2/2016 |
| CN | 107613897 A | 1/2018 |
| EP | 3069679 A1 | 9/2016 |
| WO | 2006079211 A1 | 8/2006 |
| WO | 2009116535 A1 | 9/2009 |
| WO | 2016066287 A1 | 5/2016 |

SYSTEMS AND METHODS FOR PERFORMING INTRAOPERATIVE GUIDANCE

CROSS-REFERENCE TO RELATED APPLICATION

This application claims priority to U.S. Provisional Patent Application No. 62/655,102, titled "SYSTEMS AND METHODS FOR PERFORMING INTRAOPERATIVE GUIDANCE" and filed on Apr. 9, 2018, the entire contents of which is incorporated herein by reference, and to U.S. Provisional Patent Application No. 62/736,348, titled "SYSTEMS AND METHODS FOR PERFORMING INTRAOPERATIVE GUIDANCE" and filed on Sep. 25, 2018, the entire contents of which is incorporated herein by reference.

BACKGROUND

The present disclosure relates to navigated medical procedures.

Navigation enables the surgeon to visualize the position and orientation of a medical instrument relative to the anatomy of a patient. In order to visualize the position and orientation of the medical instrument, fiducial markers are attached to the medical instrument such that signals from the fiducial markers can be detected by cameras or other sensing devices (e.g. electromagnetic tracking devices), and the position and orientation of the medical instrument can be triangulated.

SUMMARY

Systems and methods are provided in which an intraoperative video feed is augmented with one or more virtual display features based on a detected orientation and position of the tracked medical instrument. In some example embodiments, the virtual display features may be employed to represent, in an augmented video feed, information associated with a previously-detected intraoperative position and orientation of the tracked medical instrument. The virtual display element may be employed, for example, to facilitate the alignment of an untracked medical instrument with a previously determined intraoperative position and orientation of the tracked medical instrument. In other example embodiments, the virtual display element may be dynamically displayed in a fixed spatial relationship relative to the tracked medical instrument.

Accordingly, in a first aspect, there is provided a method of providing intraoperative guidance for aligning an untrackable medical instrument during a medical procedure, the method comprising:
  employing a tracking system to detect signals from fiducial markers associated with a trackable medical instrument;
  processing the signals to determine, in a frame of reference associated with the tracking system, an intraoperative orientation and position of the trackable medical instrument;
  employing a camera to obtain an intraoperative video feed;
  displaying the intraoperative video feed; and
  during a subsequent phase of the medical procedure involving the untrackable medical instrument, employing a coordinate transformation between a frame of reference associated with the camera and the frame of reference associated with the tracking system to augment the intraoperative video feed with a virtual display feature identifying the previously determined intraoperative orientation and position of the trackable medical instrument, thereby enabling, during the subsequent phase of the medical procedure, visual alignment of the untrackable medical instrument relative to the previously determined intraoperative orientation and position of the trackable medical instrument.

In another aspect, there is provided a method of providing intraoperative guidance for aligning an untrackable medical instrument during a medical procedure, the method comprising:
  employing a surface detection system to detect signals from one or more surface fiducial features associated with a trackable medical instrument;
  processing the signals to determine an intraoperative orientation and position of the trackable medical instrument;
  employing a camera of the surface detection system to obtain an intraoperative video feed;
  displaying the intraoperative video feed; and
  during a subsequent phase of the medical procedure involving an untrackable medical instrument, augmenting the intraoperative video feed with a virtual display feature associated with the previously determined intraoperative orientation and position of the trackable medical instrument, thereby enabling, during the subsequent phase of the medical procedure, visual alignment of the untrackable medical instrument relative to the previously determined intraoperative orientation and position of the trackable medical instrument.

In another aspect, there is provided a method of providing intraoperative guidance for aligning an untrackable medical instrument during a medical procedure, the method comprising:
  employing a tracking system to detect signals from fiducial markers associated with a trackable medical instrument;
  processing the signals to determine an intraoperative orientation and position of the trackable medical instrument;
  employing a camera of the tracking system to obtain an intraoperative video feed;
  displaying the intraoperative video feed; and
  during a subsequent phase of the medical procedure involving an untrackable medical instrument, augmenting the intraoperative video feed with a virtual display feature associated with the previously determined intraoperative orientation and position of the trackable medical instrument, thereby enabling, during the subsequent phase of the medical procedure, visual alignment of the untrackable medical instrument relative to the previously determined intraoperative orientation and position of the trackable medical instrument.

In another aspect, there is provided a method of aligning an untrackable medical instrument during a medical procedure, the method comprising:
  intraoperatively orienting and positioning a trackable medical instrument in an intraoperative orientation and position relative to a patient;
  employing a navigation and tracking system to:
    detect signals from fiducial markers associated with the trackable medical instrument;
    process the signals to determine, in a frame of reference associated with the tracking system, an intraoperative orientation and position of the trackable medical instrument;

employ a camera to obtain an intraoperative video feed;
display the intraoperative video feed
employ a coordinate transformation between a frame of reference associated with the camera and the frame of reference associated with the tracking system to augment the intraoperative video feed with a virtual display feature associated with the determined intraoperative position and orientation of the trackable medical instrument; and during a subsequent phase of the medical procedure involving the untrackable medical instrument, viewing the intraoperative video feed and employing the virtual display feature to position and orient the untracked medical instrument.

In another aspect, there is provided a method of providing intraoperative guidance during a surgical procedure, the method comprising:
employing a tracking system to detect signals from fiducial markers associated with a trackable medical instrument;
processing the signals to determine, in a frame of reference associated with the tracking system, an intraoperative orientation and position of the trackable medical instrument;
employing a camera to obtain an intraoperative video feed;
displaying the intraoperative video feed; and
employing a coordinate transformation between a frame of reference associated with the camera and the frame of reference associated with the tracking system to augment the intraoperative video feed in real time with a virtual display feature associated with the trackable medical instrument.

In another aspect, there is provided a system for providing intraoperative guidance for aligning an untrackable medical instrument during a medical procedure, the system comprising:
a tracking subsystem
a display; and
computer hardware operatively coupled to said tracking subsystem, wherein said computer hardware comprises memory coupled with one or more processors to store instructions, which when executed by the one or more processors, causes the one or more processors to perform operations comprising:
employing said tracking subsystem to detect signals from fiducial markers associated with a trackable medical instrument;
processing the signals to determine, in a frame of reference associated with the tracking system, an intraoperative orientation and position of the trackable medical instrument;
employing a camera to obtain an intraoperative video feed;
displaying the intraoperative video feed on the display; and
during a subsequent phase of the medical procedure involving the untrackable medical instrument, employing a coordinate transformation between a frame of reference associated with the camera and the frame of reference associated with the tracking system to augment the intraoperative video feed with a virtual display feature identifying the previously determined intraoperative orientation and position of the trackable medical instrument, thereby enabling, during the subsequent phase of the medical procedure, visual alignment of the untrackable medical instrument relative to the previously determined intraoperative orientation and position of the trackable medical instrument.

In another aspect, there is provided a system for providing intraoperative guidance during a surgical procedure, the system comprising:
a tracking subsystem;
a display; and
computer hardware operatively coupled to said tracking subsystem, wherein said computer hardware comprises memory coupled with one or more processors to store instructions, which when executed by the one or more processors, causes the one or more processors to perform operations comprising:
employing said tracking subsystem to detect signals from fiducial markers associated with a trackable medical instrument;
processing the signals to determine, in a frame of reference associated with the tracking system, an intraoperative orientation and position of the trackable medical instrument;
employing a camera to obtain an intraoperative video feed;
displaying the intraoperative video feed on the display; and
employing a coordinate transformation between a frame of reference associated with the camera and the frame of reference associated with the tracking system to augment the intraoperative video feed in real time with a virtual display feature associated with the trackable medical instrument.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
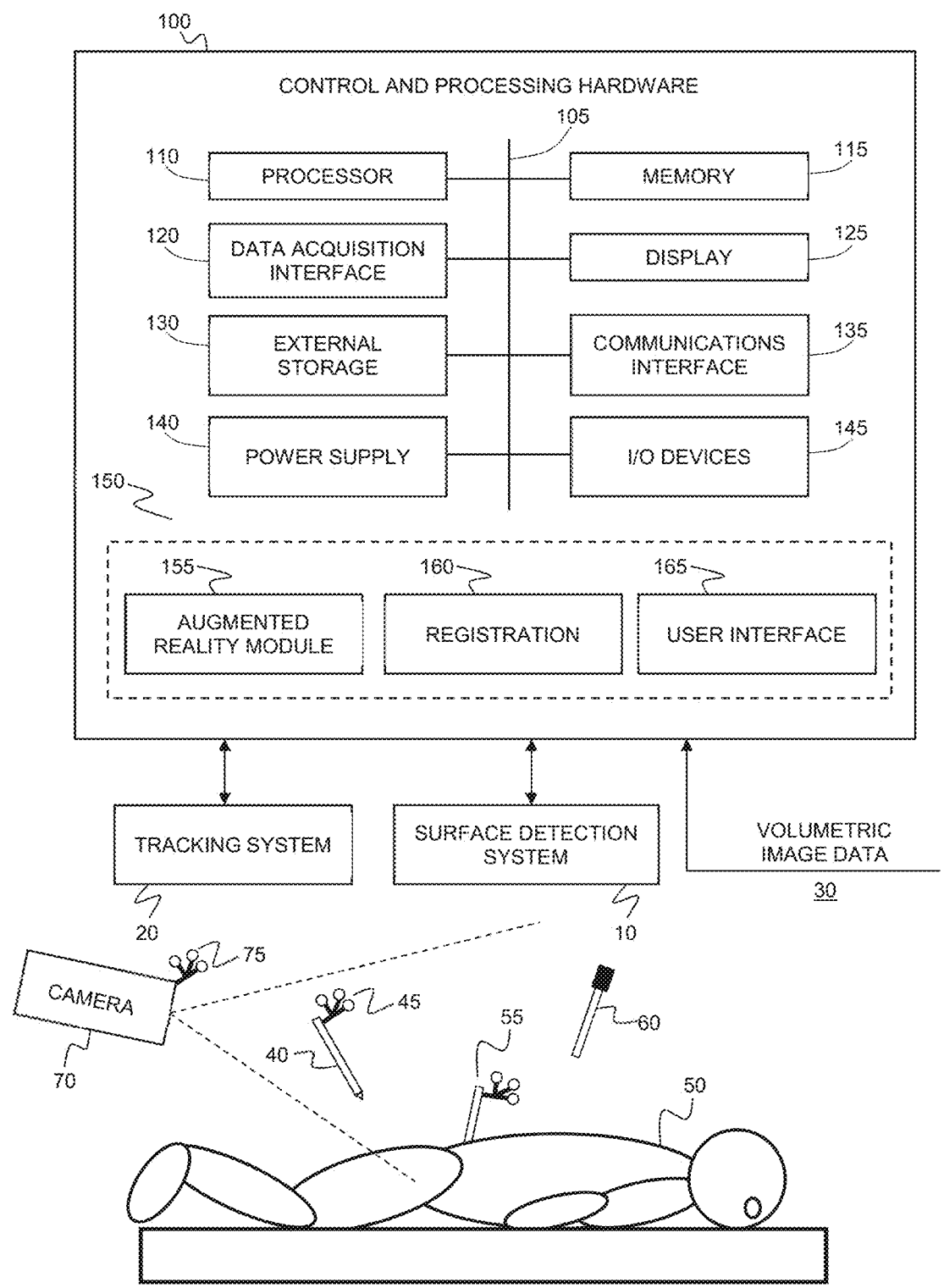
FIG. 1 shows an example system for providing intraoperative guidance of trackable and untrackable medical instruments.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Most surgical procedures typically utilize a large number of different medical instruments to implement a surgical plan. Although some medical instruments may be tracked by a tracking system via the detection of signals from fiducial markers (fiducials), it is typically the case that only a subset of the medical instruments employed during a procedure are tracked by the navigation system. For example, during a given medical procedure, it is common to employ medical instruments (e.g. surgical instruments) that are provided by a variety of different manufacturers, while only some of the medical instruments may be trackable using a given tracking system. It therefore follows that a technical problem exists in the art whereby only a subset of medical instruments employed during a medical procedure are trackable and suitable for representation in a navigation display (e.g. navigation user interface window).

Various aspects of the present disclosure provide solutions to this problem by augmenting an intraoperative video feed with one or more virtual display features based on a detected orientation and position of the tracked medical instrument. In some example embodiments, the virtual display features may be employed to represent, in an augmented video feed, information associated with a previously-detected intraoperative position and orientation of the tracked medical instrument. The virtual display element may be employed, for example, to facilitate the alignment of an untracked medical instrument with a previously determined intraoperative position and orientation of the tracked medical instrument. In another example application, a user or clinician may initially position and align an untracked medical instrument in a given position and orientation that is believed to be a correct intraoperative position and orientation, and then view the position and orientation of the untracked medical instrument in the augmented video feed relative to the virtual display element, in order to determine whether or not the current position and orientation is indeed aligned relative to the previously-detected intraoperative position and orientation of the tracked medical instrument. In other example embodiments, the virtual display element may be dynamically displayed in a fixed spatial relationship relative to the tracked medical instrument.

Referring now to FIG. 1, an example system is shown for determining an intraoperative orientation of a tracked medical instrument and augmenting an intraoperative video feed based the detected orientation and position of the tracked medical instrument. Although the present example system includes a surface detection system to facilitate the registration of volumetric image data with the patient in an intraoperative frame of reference, other systems and methods may be employed in the alternative. For example, in one alternative implementation, an intraoperative CT scan may be performed with a reference array of fiducial marker locations attached to the patient to facilitate direct intraoperative registration of volumetric image data with the patient. The example system includes a surface detection system 10 that is operably interfaced with control and processing hardware 100. The surface detection system 10 may be any suitable system for detecting, measuring, imaging, or otherwise determining the surface topography of one or more objects (such as, but not limited to, a region of an exposed spine of a patient 50). According to the present non-limiting example embodiment, the intraoperative video feed (or multiple intraoperative video feeds) is obtained from one or more cameras of the surface detection system 10. Non-limiting examples of suitable surface detection systems include photogrammetry systems, stereo vision systems, and structured light detection systems.

The example system shown in FIG. 1 also includes a tracking system 20, which may be employed to track the position and orientation of one or more trackable medical instruments 40. The trackable medical instrument 40 is shown having fiducial markers 45 attached thereto, and passive or active signals emitted or reflected (e.g. scattered) from the fiducial markers 45 are detected by the tracking system 20 (e.g. a stereoscopic tracking system employing two tracking cameras).

In one example embodiment, the optical tracking subsystem 20 may include stereo cameras with integrated infrared illumination. Due to their high reflectivity to infrared light, the fiducial markers 45 can be easily localized in each image of the two cameras. These image positions can be employed to calculate the three-dimensional position of each fiducial marker 45 by geometrical triangulation. The triangulation process can be performed, for example, by first calculating the center of mass of each of the detected markers in both camera views of the stereo calibrated camera system. This yields a set of marker points in both camera views from which the disparity between corresponding points in both views can then be calculated. This disparity along with the x and y pixel locations of each marker in one of the camera views can then be transformed into a three-dimensional spatial coordinate (in a coordinate system of the tracking system 20) using a perspective transformation. If at least three fiducial markers 45 are rigidly attached to medical instrument 40, it is possible to compute its position and orientation (the six degrees of freedom).

In some example illustrations provided herein, the fiducial markers 45 for the optical tracking system are shown as reflective spheres, which are commonly used for passive optical tracking. However, any other type of markers, or marker attributes, can be used depending on the used tracking system such as, but not limited to, active markers (i.e. LEDs, which do not require integration of additional lighting and electromagnetic markers) and passive markers (e.g. glyphs, varying marker color, varying marker size, varying marker shape). It is to be understood that in some embodiments, less than three markers may be employed for position and location tracking. For example, a single marker may be provided for position and location tracking, provided that the single marker includes sufficient spatial structure and/or content. An example of such a single marker is a glyph including co-planar spatial features such as corner or edge features.

While FIG. 1 illustrates an example system having two subsystems (tracking and surface detection), it is noted that alternative system configurations may be employed to perform simultaneous tracking and acquisition of anatomical surfaces using an integrated system, for example, as described in International Patent Application No. PCT/CA2011/050257, which is hereby incorporated by reference in its entirety.

FIG. 1 also illustrates an example implementation of control and processing hardware 100, which includes one or more processors 110 (for example, a CPU/microprocessor), bus 105, memory 115, which may include random access memory (RAM) and/or read only memory (ROM), a data acquisition interface 120, a display 125, external storage 130, one more communications interfaces 135, a power supply 140, and one or more input/output devices and/or interfaces 145 (e.g. a speaker, a user input device, such as a keyboard, a keypad, a mouse, a position tracked stylus, a position tracked probe, a foot switch, and/or a microphone for capturing speech commands).

It is to be understood that the example system shown in FIG. 1 is illustrative of a non-limiting example embodiment and is not intended to be limited to the components shown. Furthermore, one or more components of the control and processing hardware 100 may be provided as an external component that is interfaced to a processing device. For example, as shown in the figure, one or both of the surface detection system 10 and the tracking system 20 may be included as a component of control and processing hardware 100, or may be provided as one or more external devices.

Although only one of each component is illustrated in FIG. 1, any number of each component can be included in the control and processing hardware 100. For example, a computer typically contains a number of different data storage media. Furthermore, although bus 105 is depicted as a single connection between all of the components, it will be appreciated that the bus 105 may represent one or more circuits, devices or communication channels which link two or more of the components. For example, in personal computers, bus 105 often includes or is a motherboard. Control and processing hardware 100 may include many more or less components than those shown.

Control and processing hardware 100 may be implemented as one or more physical devices that are coupled to processor 110 through one of more communications channels or interfaces. For example, control and processing hardware 100 can be implemented using application specific integrated circuits (ASICs). Alternatively, control and processing hardware 100 can be implemented as a combination of hardware and software, where the software is loaded into the processor from the memory or over a network connection.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine-readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refer to all computer-readable media, except for a transitory propagating signal per se.

Embodiments of the present disclosure can be implemented via processor 110 and/or memory 115. For example, the functionalities described below can be partially implemented via hardware logic in processor 110 and partially using the instructions stored in memory 115. Some embodiments are implemented using processor 110 without additional instructions stored in memory 115. Some embodiments are implemented using the instructions stored in memory 115 for execution by one or more microprocessors, which may be general purpose processors or specialty purpose processors. Thus, the disclosure is not limited to a specific configuration of hardware and/or software.

The control and processing hardware 100 is programmed with subroutines, applications or modules 150, that include executable instructions, which when executed by the one or more processors 110, causes the system to perform one or more methods described in the present disclosure. Such instructions may be stored, for example, in memory 115 and/or other internal storage.

For example, as described in detail below, the augmented reality module 155 of the control and processing hardware 100 may be employed to augment one or more intraoperative video feeds, obtained from video data obtained from one or more cameras of the surface detection system 10, or one or more additional cameras, with one or more virtual display elements based on an intraoperative orientation and position of a trackable medical probe that is determined via the tracking system 20.

The navigation user interface module 165 includes executable instructions for displaying a user interface for performing, for example, image-guided surgical procedure and for displaying one or more intraoperative video feeds.

Furthermore, in the example embodiment shown, the registration module 160 includes executable instructions for registering segmented surface data (obtained from the volumetric image data 30) with intraoperative surface data that is obtained using the surface detection system 10, as described above. For example, the volumetric image data 30 may be provided to the control and processing hardware 100 for registration to intraoperatively acquired surface data.

The registration module 160 performs image registration between a segmented surface generated from the volumetric image data 30 and the intraoperative surface data. Non-limiting examples of surface segmentation methods include non-template-based methods and methods which utilize anatomical shape models. Non-template-based methods can utilize geometrical properties, such as connectivity, surface normals, and curvatures to determine the boundary of the segmented region, or statistical properties, such as variance from nearby neighboring points on the surface. Methods based on anatomical shape models can utilize a pre-computed atlas (e.g. of vertebra) as a template to perform the segmentation. Both classes of method can also be used in combination. In all these methods, one or more volumetric fiducial points can serve as a seed point to initialize the segmentation process. Alternatively, for segmentation methods which are fully automatic and operate on the entire volumetric data (which are usually based on anatomical atlases), one or more volumetric fiducials can be used to tag the level(s) of interest.

Surface registration may be performed as an initial registration based on correspondence between volumetric fiducial points defined in the volumetric image data 30 and respective intraoperative fiducial points identified on a segmented surface. After generating the initial registration, a surface-to-surface registration may then be performed, between the segmented surface data and the intraoperative surface data, thereby obtaining a registration transform. The registration transform maps the segmented surface in the volumetric frame of reference to the intraoperative surface data. It will be understood that any suitable surface registration method may be employed to perform registration between surfaces, when performing methods according to the example embodiments disclosed herein. Non-limiting examples of suitable registration methods include the iterative closest point algorithm, wherein the distance between points from difference surfaces are minimized.

In the example case in which the surface detection system 10 is a structured light detection system, a projection device is employed to project surface topography detection light onto a region of interest, and one or more cameras detect surface topography light that is scattered or reflected from the region of interest. The detected optical signals can be used to generate surface topography datasets consisting of point clouds or meshes. More specifically, the projection device projects temporally and/or spatially modulated light onto the surface to be imaged, while the camera(s) capture images of the illuminated surface. This active illumination enables robust and efficient identification of pixel correspondences between calibrated camera-projector (a projector may be thought of as an inverse camera) or calibrated camera-camera system. The correspondence (disparity) data can then be transformed into real-space coordinate data in the coordinate system of the calibrated camera(s) and/or projector(s) by geometrical triangulation. During a surgical procedure, the structured light detection system may be positioned such that three-dimensional surface of the surgical site (e.g. the bony surfaces of an exposed spine) is acquired. The created virtual representation of the three-dimensional surface is then registered to volumetric image data 30 (e.g. CT, MRI, US, PET, etc.) by registration module 160, using, for example, methods described in International Patent Application No. PCT/CA2011/050257. The volumetric image data 30 may be pre-operatively acquired but is not necessarily pre-operatively acquired. For example, in some applications, the volumetric image data 30 may also be intraoperatively acquired.

In order to represent a trackable medical instrument in a navigation image, a calibration transformation is determined between the reference frames of the surface detection system 10 and the reference frame of the tracking system 20. If the relative position of the tracking system and the surface imaging system is fixed, this calibration may be performed by obtaining the position of at-least 3 points from a calibration object from both systems, and aligning these points to obtain the calibration transformation, as described in International Patent Application No. PCT/CA2011/050257.

In an alternative embodiment, as disclosed in International Patent Application No. PCT/CA2011/050257, the surface detection device may have fiducial markers attached thereto, and the fiducial markers may be tracked by the tracking system. In this configuration, a calibration procedure can be employed to obtain the calibration transformation from the frame of reference of the surface detection system to the frame of reference of the tracking system using the attached fiducial markers. The calibration transformation between the coordinate system of the tracking system and the surface imaging system is then continuously updated as the position of surface imaging device is changed.

After performing calibration, the calibration transformation between the coordinate system of the tracking system and the surface imaging system is known. Registering the surface datasets and volumetric image data is therefore equivalent to identifying the position of the volumetric image data in the coordinate system of the tracking system. As a result, any trackable medical instrument 40, which is afterwards tracked with the tracking subsystem, can be presented to the surgeon as an overlay of the medical instrument 40 on the registered 3D image data on a display or other visualization devices.

To compensate for patient or system motion, it is also advantageous to use a tracked device attached to the patient's anatomy (e.g. to a skeletal feature of the patient's anatomy). Accordingly, as shown in FIG. 1, the position of a tracking marker support structure 55 is recorded by the tracking system at the same time (i.e. within a time duration that is sufficiently small to preclude errors associated with patient motion) as when the surface dataset is acquired. The surface dataset is transformed to the coordinate system of tracking system (using the previously acquired calibration transformation) and is then registered to the volumetric image data. Subsequent tracking of medical instruments relative to the volumetric image data can be performed based on the tracked tracking marker support structure, with compensation for patient or system motion, without the need for continuous acquisition of surface data.

In one example embodiment, as described in International PCT Patent Application No. PCT/CA2015/050939, titled "TRACKING MARKER SUPPORT STRUCTURE AND SURFACE REGISTRATION METHODS EMPLOYING THE SAME FOR PERFORMING NAVIGATED SURGICAL PROCEDURES" and filed on Sep. 23, 2015, which is hereby incorporated by reference in its entirety, the tracking marker support structure 55 is employed to compute a real-time calibration transformation between the tracking system and the surface imaging system, for example, to assess the validity of the previously determined calibration transformation. As described below, this can be achieved by performing surface detection to determine the position and orientation of the tracking marker support structure in the reference frame of the surface imaging system, and comparing this position with the position of the tracking marker support structure that is determined by the tracking system based on the detection of signals from the markers, where the comparison employs the last calibration transformation (the previously determined calibration transformation). The validity of the last calibration transformation can therefore be assessed by determining whether or not the computed position and orientation are within a prescribed tolerance.

This method may be performed at any time before or during a surgical procedure, such as at each time registration is performed, and optionally each time a tracking marker support structure is attached to a new skeletal feature of a patient. For example, in the case of a spinal surgical procedure, the method may be performed or repeated when the tracking marker support structure (or an additional tracking marker support structure) is attached to a new vertebral level. This method will be referred to herein as "active calibration".

Referring again to FIG. 1, a typical medical procedure may involve the use of both trackable medical instruments, such as trackable medical instrument 40, and also untrackable medical instruments, such as untrackable medical instrument 60. While the tracking system 20 is capable of tracking the trackable medical instrument 40, such that the trackable medical instrument 40 is displayable relative to volumetric image data associated with the patient on navigation images, the system is effectively blind to the presence of untrackable medical instruments 60.

Despite the inability of the system to track the untrackable instruments 60, the untrackable instrument is nonetheless viewable by a clinical or operator in an intraoperative video feed. Recognizing that the intraoperative positions and orientations of untracked medical instruments are often related to the intraoperative positions and orientations of a tracked medical instrument during a previous (earlier) phase or step of a medical procedure, the present inventors realized that if the intraoperative video feed is generated using a camera having a frame of reference that is related to a frame of reference of the tracking system (via a known coordinate transformation), then it is possible to augment the intraoperative video feed with one or more virtual display features based on a detected orientation and position of the tracked medical instrument, such that the one or more virtual display features shown in the intraoperative video feed may be employed to facilitate the subsequent alignment of an untracked medical instrument.

Accordingly, in some example embodiments, one or more virtual display features may be employed to represent, in an augmented video feed, information associated with a previously-detected intraoperative position and orientation of a tracked medical instrument, where a coordinate transformation is known between the frame of reference of the video camera used to generate the intraoperative video feed and the tracking system. As described below, the virtual display element may be employed, for example, to facilitate the alignment of an untracked medical instrument.

Figure 2:
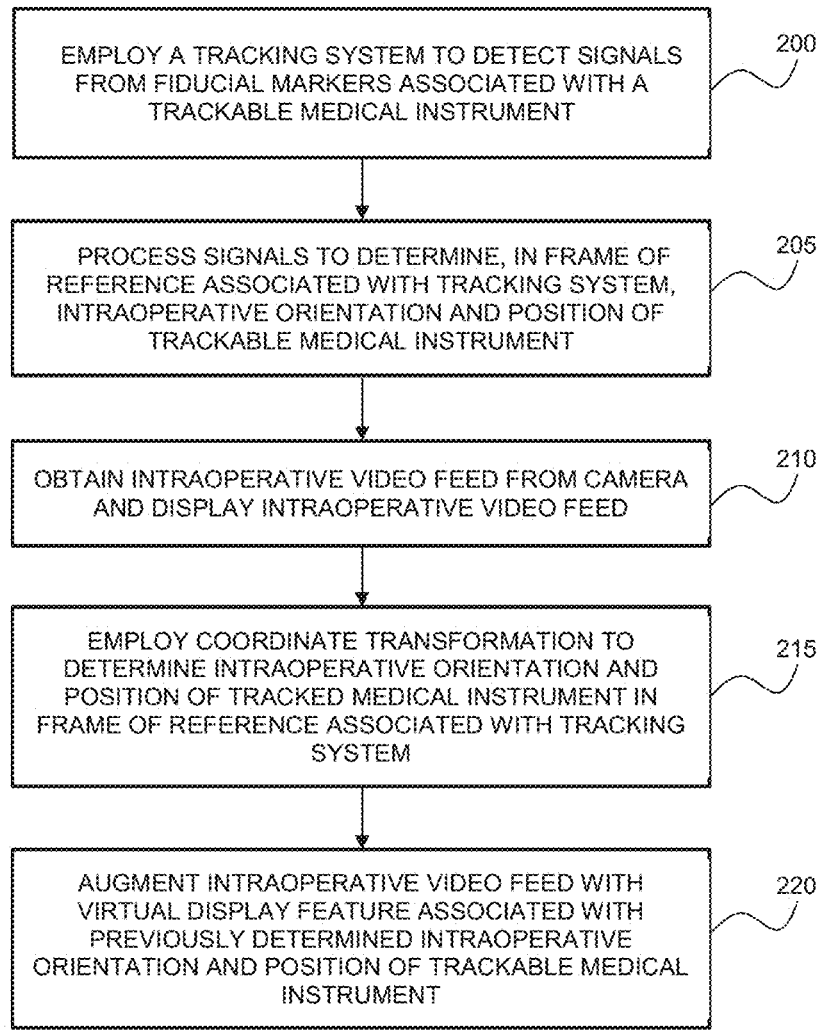
FIG. 2 is a flow chart illustrating an example method of providing intraoperative guidance, in which an intraoperative video feed is augmented with a virtual display feature associated with the detected intraoperative orientation and position of a trackable medical instrument.

FIG. 2 provides a flow chart illustrating such an example embodiment. In step 200, a tracking system is employed to detect signals from fiducial markers associated with a trackable medical instrument. This step may be performed when the medical instrument is in a specific intraoperative orientation and position that defines a reference intraoperative orientation and position which is relevant to a subsequent step during the medical procedure. As described in further detail below, and example of such a reference intraoperative orientation and position is the orientation and of position of a pedicle probe during a cannulation operation, which defines an intraoperative axis that is relevant during latter stages of the medical procedure, such as during taping of the cannulated trajectory and insertion of the pedicle screw. The signals are processed in step 205 to determine, in a frame of reference associated with the tracking system, an intraoperative orientation and position of the trackable medical instrument.

For example, as described above, the images of the detected fiducial marker signals can be employed to calculate the three-dimensional position of each fiducial marker 45 by geometrical triangulation, and since the fiducial markers are arranged in a fixed spatial relationship relative to the trackable medical instrument, the position and orientation of the trackable medical instrument can be determined (e.g. using a known geometrical model of at least a portion of the trackable medical instrument and relative locations of the fiducial markers).

In step 210, a camera is employed to generate an intraoperative video feed, which is then intraoperatively displayed (e.g. on a display window of a navigation user interface). The camera is configured such that a coordinate transformation is known between the frame of reference of the camera and the frame of reference of the tracking system.

In step 215, the intraoperative orientation and position of the trackable medical instrument, as determined in step 205, is transformed into the frame of reference of the tracking system, using the known coordinate transformation between the frame of reference of the camera and the frame of reference of the tracking system. Having transformed the intraoperative orientation and position of the trackable medical instrument into the frame of reference of the tracking system, the intraoperative video feed may be augmented with display information, such as a virtual display feature, that is associated with the intraoperative orientation and position of the trackable medical instrument. For example, the intraoperative video feed may be augmented with a virtual display feature identifying the previously determined intraoperative orientation and position of the trackable medical instrument, as shown at step 220.

The preceding method may be employed to facilitate the alignment of an untracked medical instrument, during a later phase (stage, time, step or event) of a medical procedure, with the intraoperative orientation and position of the trackable medical instrument during an earlier phase of the medical procedure. By augmenting the intraoperative video feed with the virtual display feature that is indicative of the previously determined orientation and position of the trackable medical instrument, a surgeon or other medical practitioner may view the intraoperative video feed and align an untrackable medical instrument relative to the virtual display feature.

For example, as described in the examples provided below, the present example embodiment may be employed to assist the positioning of one or more untrackable medical instruments during a medical procedure involving the implantation of a pedicle screw. For example, the intraoperative orientation and position of a tracked pedicle probe may be detected and stored using a tracking system. During a subsequent phase of the medical procedure, an intraoperative video feed may be augmented, according to the example method described above, with a virtual display feature that is indicative of the previously determined intraoperative orientation and position of the pedicle probe. One or more untracked medical instruments, such as a tap or a screwdriver, may subsequently be visually aligned to the virtual display feature while viewing the augmented intraoperative video feed.

Figure 3A:
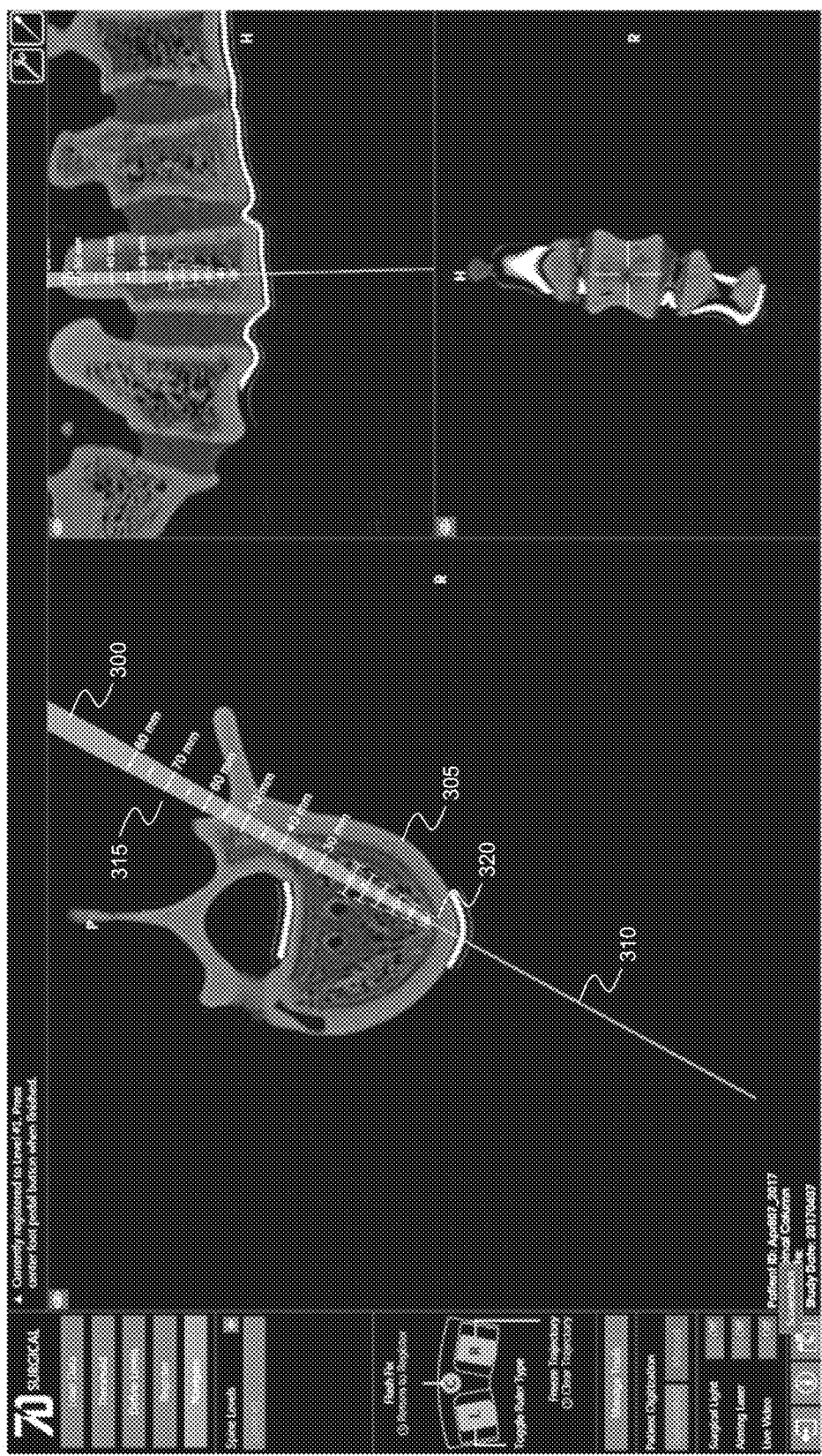
FIG. 3A shows an example of a navigation user interface displaying different intraoperative views of a tracked medical instrument relative to volumetric images, where a pedicle probe is shown inserted into a pedicle.

Referring now to FIGS. 3A-3B and 4A-4C, and example implementation of the method shown in FIG. 2 is illustrated for the clinical application of pedicle screw placement. During a medical procedure involving pedicle screw placement, trackable medical instruments, such as a trackable awl and a trackable pedicle probe, are often used to develop the initial trajectory for the placement of the pedicle screw using a surgical navigation system, where the trackable awl is employed for the creation of an entry point, and the trackable pedicle probe is employed for cannulation along the appropriate trajectory. FIG. 3A shows an example surgical navigation user interface in which a pedicle probe 300 is shown relative to a pre-operative volumetric image 305 of the patient.

Figure 3B:
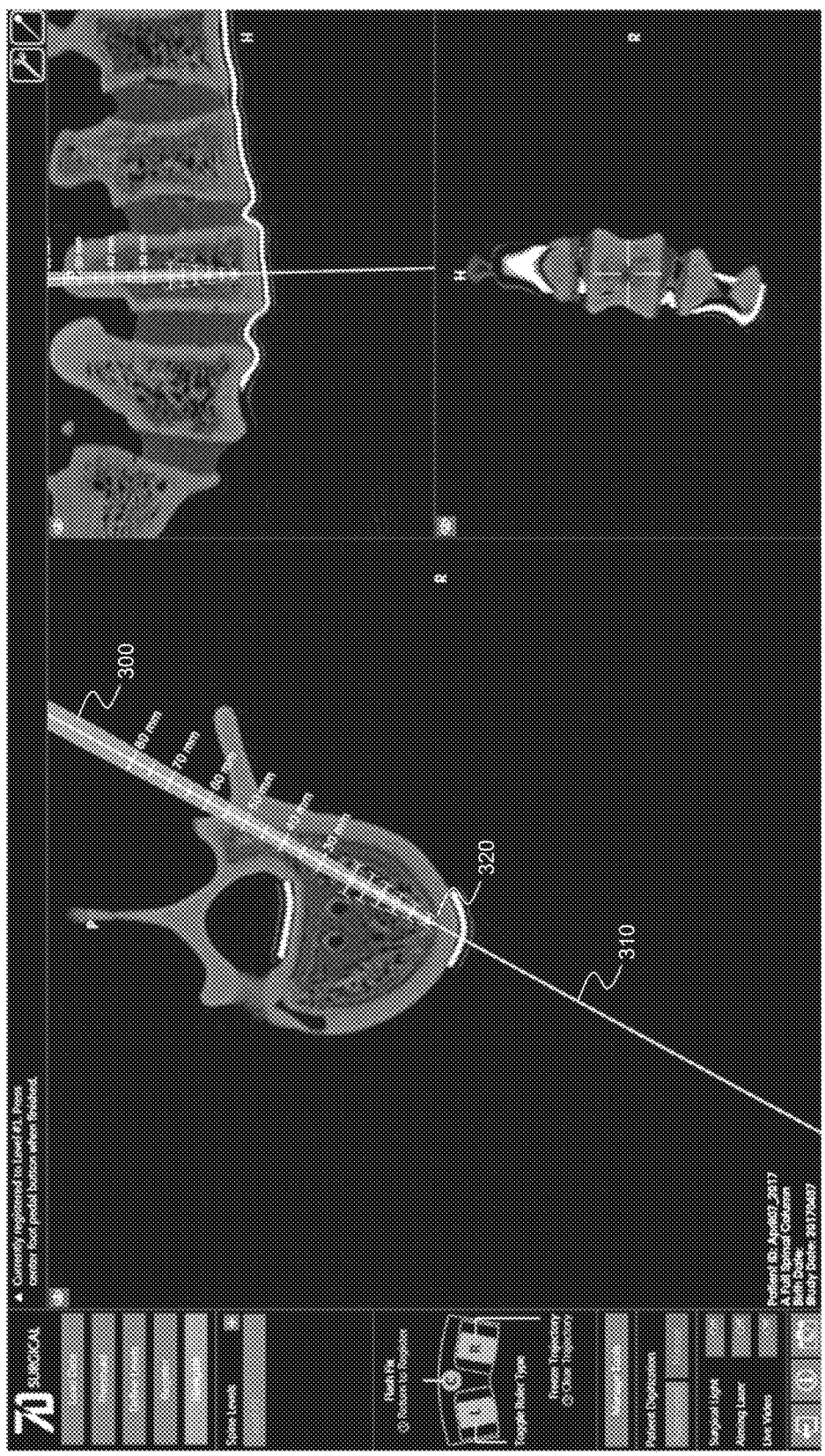
FIG. 3B shows the navigation user interface of FIG. 3A and displays a linear virtual feature associated with the detected position and orientation of the pedicle probe.

The example navigation windows shown in FIGS. 3A and 3B include spatial annotations, which can be employed to perform measurements to determine a suitable screw diameter and length, as disclosed in US Patent Publication No. 20170202626, titled "SYSTEMS AND METHODS FOR DISPLAYING GUIDANCE IMAGES WITH SPATIAL ANNOTATIONS DURING A GUIDED MEDICAL PROCEDURE" and filed on Jan. 12, 2017, which is hereby incorporated by reference in its entirety. Briefly, the guidance image shows a two-dimensional cross-section through the spinal column, where the two-dimensional image includes, and shows, the longitudinal axis 310 of the pedicle probe 300. A plurality of spatial annotations 315 are generated along the longitudinal axis 310 of the pedicle probe 300, where each spatial annotation is centered on the longitudinal axis 310. In the present example embodiment, the spatial annotations 315 are generated such that the image region (linear segment) associated with each spatial annotation extends relative to the longitudinal axis 310 in a direction that is perpendicular to the longitudinal axis. Each spatial annotation delineates (indicates) an image region (in this case, a linear image segment) that has a known length measure associated therewith. Each spatial annotation thus provides a graduation that enables the operator/user to obtain a visual measure of the relative size of anatomical and/or functional features in the guidance images.

As shown in FIG. 3A, the tracking of the pedicle probe during the cannulation operation, and the known transformation between the tracking system and the intraoperative patient reference frame (facilitated, for example, using surface detection, as described above, or via fiducial point picking using a tracked tool), enables the determination of the intraoperative orientation and position of the pedicle probe 300. FIG. 3A shows an outline of the pedicle probe 300, indicating the intraoperative orientation and position of the pedicle probe 300. The intraoperative orientation and position of the pedicle probe may be specified, stored and displayed in any suitable manner, such as, for example, via a longitudinal axis 310 characterizing the intraoperative orientation of the pedicle probe, and a distal location 320 of a distal end of the pedicle probe 300. FIG. 3B shows a navigation image in which the intraoperative longitudinal axis 310 of the pedicle probe 300 is shown extending both in a proximal and distal direction relative to the distal end of the pedicle probe.

Having determined the intraoperative orientation and position of the pedicle probe 300 during cannulation and identifying the intraoperative axis associated with the cannulation procedure, one or more intraoperative video feeds can be augmented to display one or more virtual display features associated with the intraoperative orientation and position of the pedicle probe. As explained above, the intraoperative orientation and position, as defined in the frame of reference of the tracking system, is transformed, using a coordinate transformation, into the frame of reference of the camera. The intraoperative video feed may then be augmented with the one or more virtual display features, in order to assist the clinician by representing, in the intraoperative video feed, information identifying the intraoperative orientation and position of the pedicle probe.

Figure 4A:
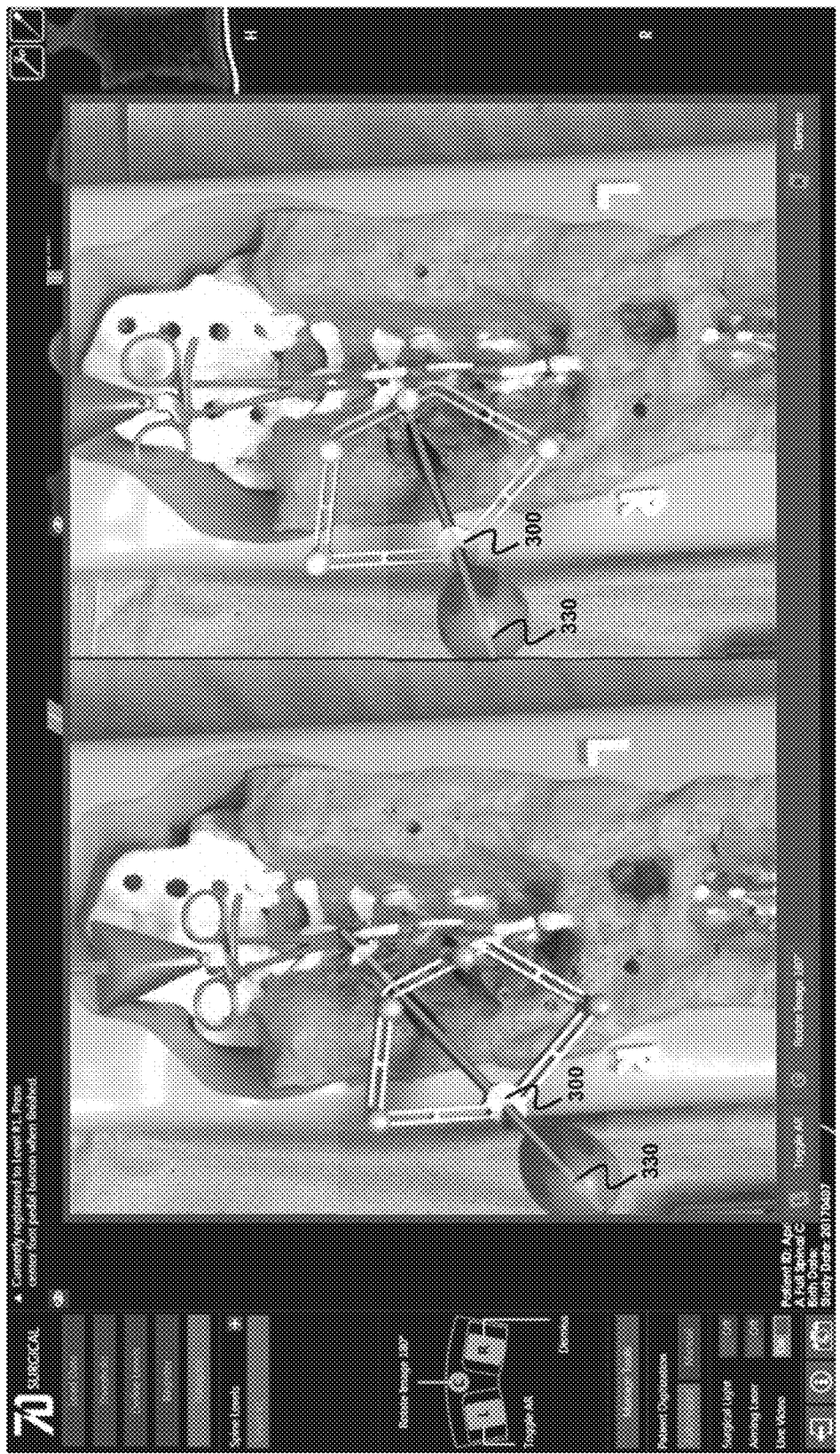
FIG. 4A shows an example frame of an intraoperative video feed obtained using two stereo cameras of a structured light surface detection system. The tracked pedicle probe can be seen in the video frames.

Referring now to FIG. 4A, an example implementation is shown in which a pair of intraoperative video feeds are generated using two cameras of the surface detection system. The two intraoperative video feeds each show the pedicle probe 300 in its intraoperative orientation and position during cannulation, and the intraoperative video feeds have been augmented with virtual display features identifying the intraoperative axis associated with the intraoperative orientation of the pedicle probe. As explained in further detail below, since a known coordinate transformation exists between the frame of reference of the surface detection system and the frame of reference of the tracking system, the intraoperative orientation and position of the tracked pedicle probe, as determined in the frame of reference of the tracking system, may be transformed and represented in the frame of reference of the surface detection system. This enables the augmentation of the intraoperative video feeds obtained from the cameras of the surface detection system. Example methods of processing the intraoperative video feeds in order to perform augmentation are described in detail below.

Figure 4B:
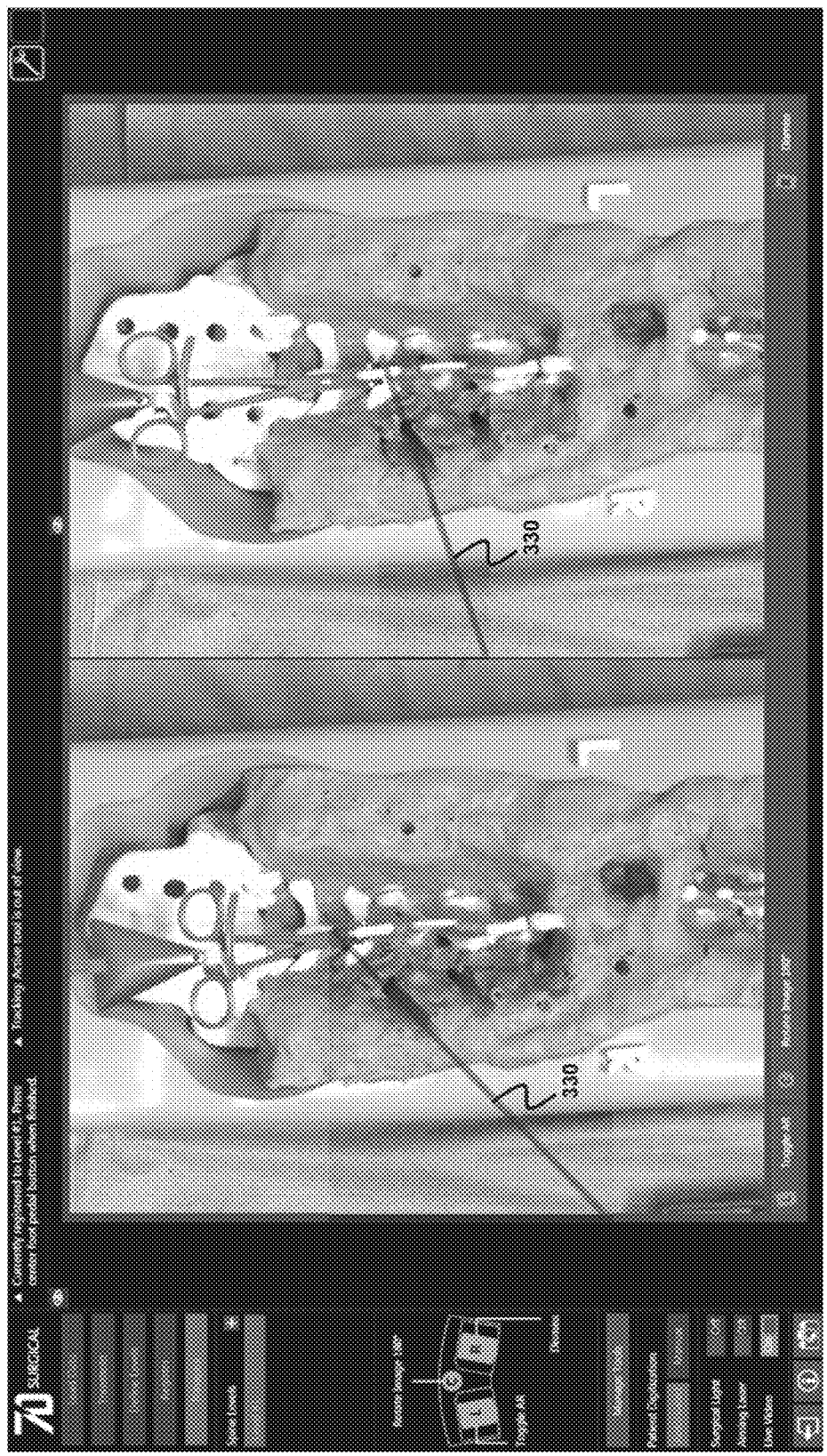
FIG. 4B shows example frames of the intraoperative video feed obtained after removal of the pedicle probe from the surgical field. The intraoperative video feed is augmented with a linear virtual display feature indicating the previously determined intraoperative position and orientation of the tracked medical instrument.
Figure 4C:
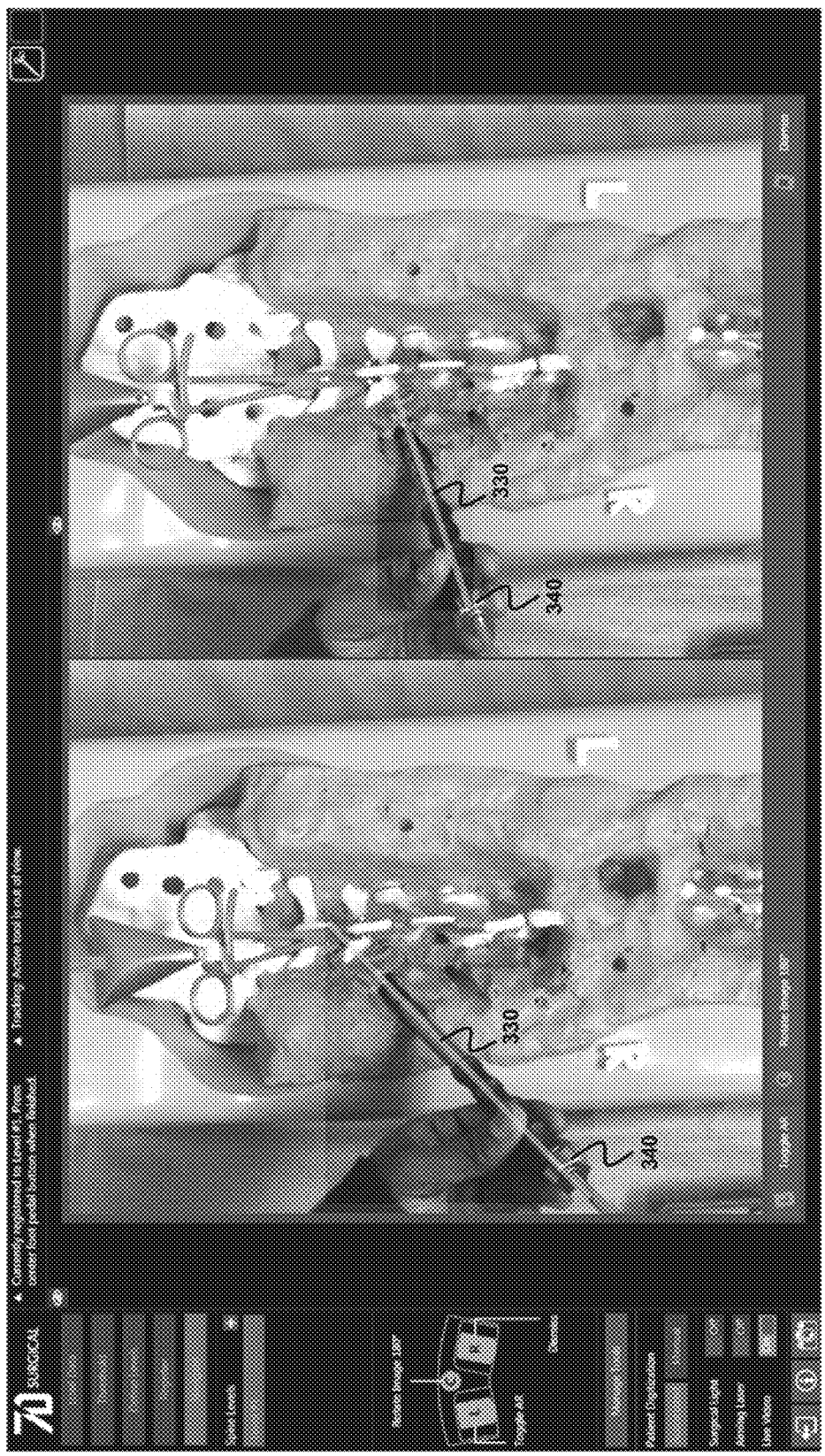
FIG. 4C shows example frames of the intraoperative video feed obtained after removal of the pedicle probe from the surgical field, where an untrackable medical instrument is shown aligned to the linear virtual display feature, such that the untrackable medical instrument is aligned with the previously determined intraoperative position and orientation of the tracked medical instrument.

In the example implementation illustrated in FIG. 4A, the virtual display feature is shown as a linear annotation 330 indicating the intraoperative orientation of the longitudinal axis of the pedicle probe 300. The linear annotation 330 is seen to align coaxially with the image of the pedicle probe 330. FIG. 4B illustrates an example implementation in which the intraoperative video feeds are augmented with the linear annotation 330 (virtual display element) after the pedicle probe has been removed from the surgical field. Furthermore, as shown in FIG. 4C, when an untrackable screwdriver 340 is introduced into the surgical field during a later phase of the medical procedure, a clinician, viewing the displayed augmented video feeds, may visually align the axis of the screwdriver 340 relative to the linear annotation 330, thereby effectively employing a previously tracked medical instrument to support the subsequent intraoperative guidance of an untrackable or untracked medical instrument.

In some example embodiments, the virtual display element may be displayed based on input from an operator, such as, for example, input including, but not limited to, voice commands, gestures or a foot pedal. In some example embodiments, the virtual display element or elements associated with a given trackable medical instrument may be displayed only when the trackable medical instrument is absent from the surgical field. In some example embodiments, the virtual display element or elements associated with a given trackable medical instrument may be displayed according to pre-selected phases of the medical procedure.

Although FIGS. 3A, 3B and 4A-4C show an example virtual display element in the form of a linear annotation, it will be understood that a virtual display element may take on many different forms. For example, in one example implementation, a virtual display element may be rendered as a shape representative of a medical instrument, such as, the trackable medical instrument associated with the detected intraoperative orientation and position, the untrackable instrument that is to be employed during a subsequent phase of the medical procedure, and/or a surgical implant that is associated with the trackable medical instrument or the untrackable medical instrument. In another example embodiment, the virtual display element may take the form of a set of collinear shapes that are discretely displayed along the intraoperative axis, such as, but not limited to, a linear array of circles. In another example implementation, the virtual display element may include a shape (e.g. a circle or arrow) indicating the distal end of the trackable medical instrument. In yet another example implementation, the virtual display element may include a directional feature (such as an arrow) indicating a direction associated with the trackable medical instrument, such as a distal direction. It will be understood that the virtual display element may provide a visual indication of the intraoperative position, the intraoperative orientation, and/or both the intraoperative orientation and position.

In some example embodiments, a plurality of virtual display elements may be displayed in the augmented video feed, where at least a subset of the plurality of virtual display elements are associated with different intraoperative orientations and positions of the trackable medical probe. In one example embodiment, two or more virtual display elements that are respectively associated with different intraoperative orientations and positions of the trackable medical probe may be displayed simultaneously. In some example embodiments, the different intraoperative orientations and positions may be associated with different surgical operations involving the trackable medical instrument. In other example embodiments, the different intraoperative orientations and positions may be associated with different time points while the trackable medical instrument is moved from one location to another location. In other example embodiments, two or more virtual display elements may be respectively associated with different trackable medical instruments.

In some example embodiments, such as the example embodiment shown in FIGS. 4A-4C, multiple annotated intraoperative video feeds may be generated and displayed, where the multiple video feeds involve different perspectives (different camera alignment) relative to the surgical field. The display of multiple augmented video feeds may be beneficial because they provide multi-directional perspectives that assist in the alignment of one or more untrackable medical instrument relative to the virtual display element. As described above, in cases in which a surface detection system is employed that has stereo cameras for surface detection, intraoperative video feeds may be generated using the two cameras of the surface detection system. Alternatively, a single intraoperative video feed can be generated based on a video feed obtained from one of the cameras or based on video feeds obtained from both cameras.

In example embodiments in which the tracking system includes two cameras that define a stereo pair, the ability of the observer to unambiguously determine the intraoperative orientation and position of the trackable medical instrument based on the position and orientation of the virtual display element in the augmented video feed may be impaired due to a proximity of the trackable medical instrument relative to a plane that includes directional axes respectively associated with the cameras (axes defined along the respective viewing directions of the cameras). In other words, if the intraoperative axis associated with the intraoperative orientation of the trackable medical instrument lies on or proximal to the baseline of the stereo camera system, a degeneracy exists that prevents the unique determination, by the observer, of the intraoperative orientation of the trackable medical instrument, based on the display of the virtual display element in the augmented video feed.

Figure 5A:
FIGS. 5A-C illustrate an example case in which a degeneracy exits in the alignment of a linear annotation and an untracked medical instrument.
Figure 5B:
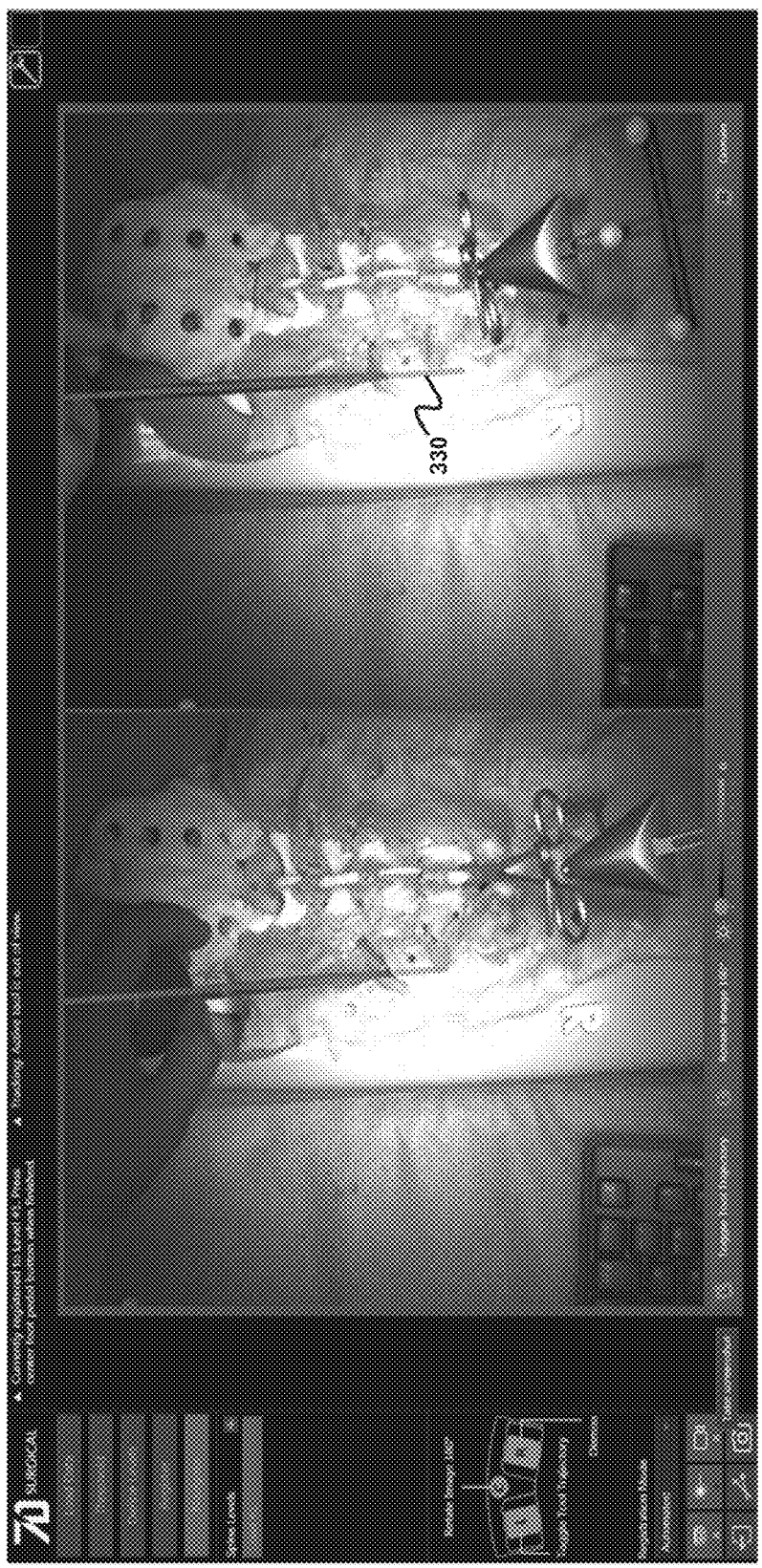
Figure 5C:
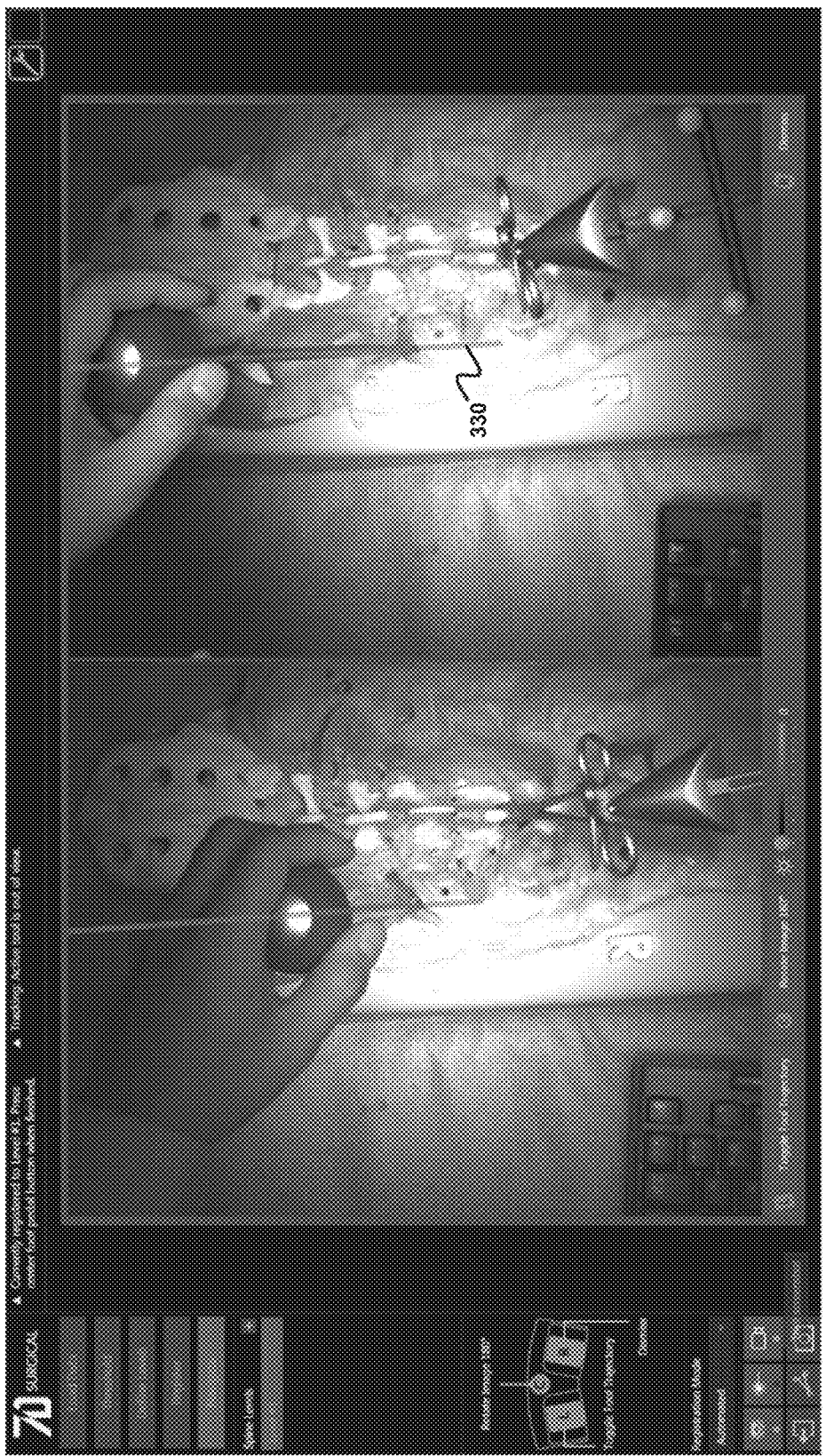

An example of such a case is shown in FIGS. 5A-5C, in which a virtual display element associated with the previously determined intraoperative position and orientation of a tracked medical instrument is shown at 330 in the form of a linear annotation along an intraoperative axis associated with the tracked medical instrument. Each of FIGS. 5A-5C also show the alignment of an untracked medical instrument to the linear annotation 330, where the vertical inclination angle of the untracked medical instrument is varied in each figure. Despite the variation of the inclination angle of the untracked medical instrument, the alignment degeneracy in the intraoperative video feeds results in each different orientation of the untracked medical instrument appearing to be aligned with the linear annotation 330. This degeneracy arises from the tracked medical instrument being aligned within the plane formed by the directional axes of the cameras.

In some example embodiments, this scenario may be prevented by detecting the degeneracy and providing an indication to an operator. The indication may instruct the operator to move and/or rotate the tracking system. For example, the indication may include a displayed or audible warning or alarm. In another example embodiment, the system may automatically rotate the tracking system in order to remove such a degeneracy, or to prevent its occurrence. In another example embodiment, such a degeneracy may be prevented or corrected by automatically repositioning the stereo camera system, such as via the control of one or more motors that are capable of translating and/or rotating the stereo camera system. The degeneracy may be detected according to many different example implementations involving the position and orientation of the intraoperative axis of the tracked medical tool relative the camera pair. For example, a degeneracy may be determined to exist when a location along the intraoperative axis that is associated with a functional end of the tracked medical instrument lies within a pre-selected spatial offset relative to the plane defined by the camera directional axes, and when an angle between the intraoperative axis and the plane defined by the camera directional axes lies within a pre-selected angular range. Alternatively, criteria associated with a degeneracy may be prescribed based on the projection of the intraoperative axis onto a plane that includes the camera baseline and is perpendicular to the plane that includes the camera directional axes.

In some example embodiments in which at least one intraoperative video feed is generated and augmented based on a video feed obtained from one or more cameras of a tracking system, one or more additional cameras (cameras that are external to the tracking system) may be employed to generate one or more additional augmented intraoperative video feeds, provided that a coordinate transformation. For example, FIG. 1 shows an example embodiment in which an additional tracked camera 70, having a set of fiducial markers 75 attached thereto, is employed to obtain an additional intraoperative video feed. The tracking of the additional camera 70 facilitates the determination of an additional coordinate transformation between a frame of reference associated with the additional camera and the frame of reference associated with the tracking system, thereby permitting the augmentation of the additional intraoperative video feed with an additional virtual display feature associated with the intraoperative orientation and position of the trackable medical instrument. The additional camera may be oriented in a non-overhead configuration. In some example implementations, one or more additional cameras may be located at the head and/or the foot of a patient support (e.g. a treatment couch or bed).

In another example embodiment, the intraoperative video feed may be generated by one or more tracked cameras, without relying on the use of cameras associated with a tracking system or cameras of a surface detection system.

In yet another example embodiment, one or more intraoperative video feeds may be generated based on video data obtained from one or more cameras of a tracking system. In such a case, since the cameras of the tracking system are used for both tracking and the generation of the one or more intraoperative video feeds, it follows that the one or more intraoperative video feeds and the tracked medical instruments reside in a common frame of reference, and a coordination transformation is not required to augment the one or more intraoperative video feeds with one or more virtual display elements associated with a tracked medical instrument.

In another example embodiment, a surface detection system may be employed for both the detection of intraoperative surface data and the tracking of medical instruments, and one or more intraoperative video feeds may be generated based on video data obtained from one or more cameras of the surface detection system. For example, a medical instrument may be tracked by the surface detection system based on one or more topographical surface fiducial features, as described, for example, in International Patent Application No. PCT/CA2011/050257 and in International PCT Patent Application No. PCT/CA2015/050939. In such a case, since the cameras of the surface detection system are used for both tracking and the generation of the one or more intraoperative video feeds, it follows that the one or more intraoperative video feeds and the tracked medical instruments reside in a common frame of reference, and a coordinate transformation is not required to augment the one or more intraoperative video feeds with one or more virtual display elements associated with a tracked medical instrument.

Figure 6:
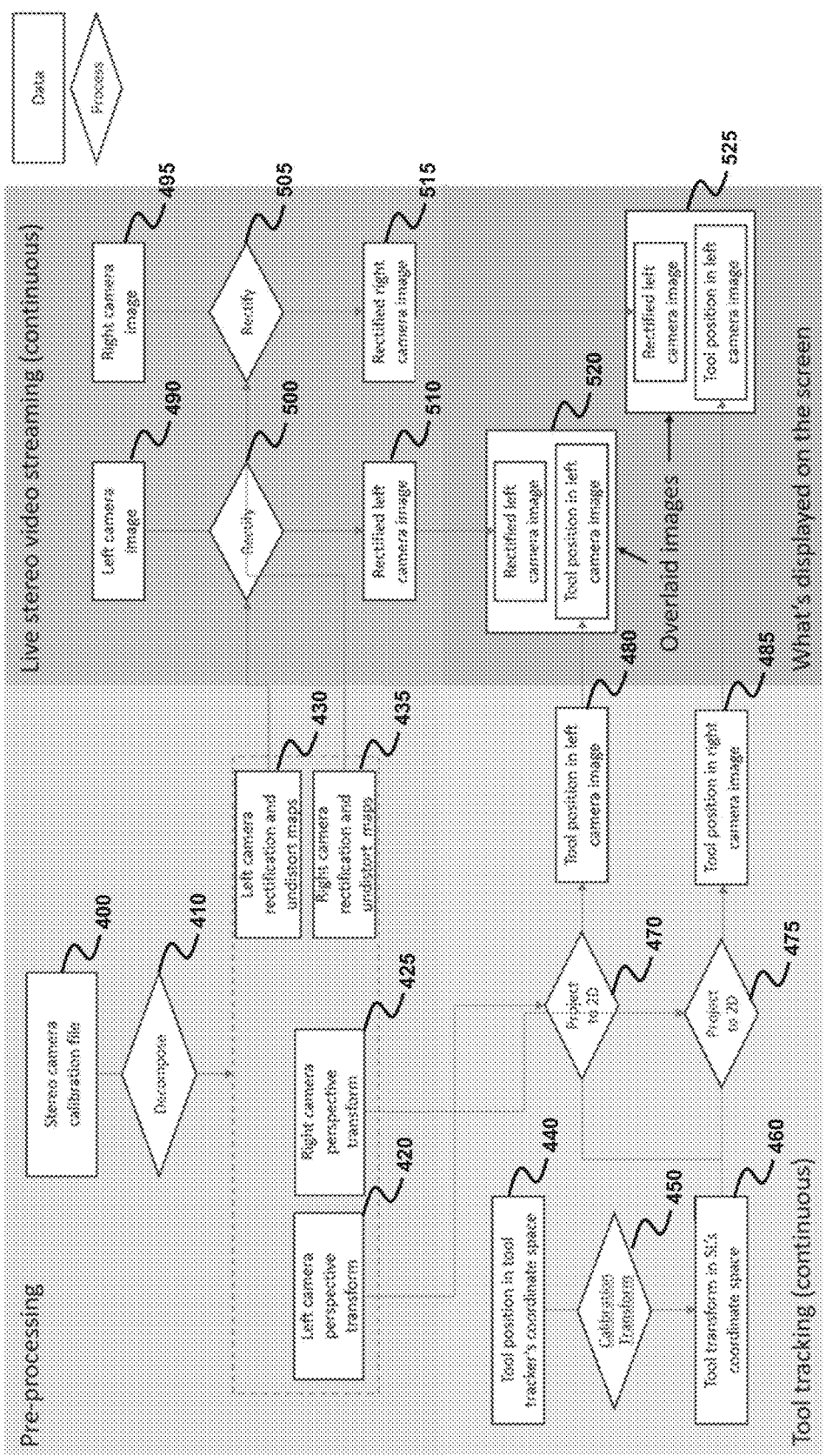
FIG. 6 is a flow chart illustrating an example process of generating and augmenting video feeds from a pair of stereo cameras.

FIG. 6 depicts an embodiment in which a structured light scanner based on a stereo rectified camera system and a tracking system are used together for the purpose of registration and navigation, as described, for example, as described in International Patent Application No. PCT/CA2011/050257. The stereo camera calibration data 400 which includes intrinsic and extrinsic parameters are used to generate perspective transforms 420 and 425 to map 3D points in the structured light imaging space on the left and right camera 2D images. The step of generating the perspective transforms 410 can practically be accomplished in the commonly used computer vision SDK OpenCV using the stereoRectify( ) function. Additionally, stereo rectification maps 430 and 435 for the left and right cameras can also be generated from said calibration data 400 in step 410 to rectify and undistort the live feeds 490 and 495 displayed to the user. In OpenCV the generation of stereo rectifications maps can be performed using the initUndistortRectifyMap ( ) function. 3D Positional data 440 from the tracking system can be transferred into the 3D coordinate system of the structured light scanner via a calibration transform 450,460, for example, using the methods described in International Patent Application No. PCT/CA2011/050257 and in International PCT Patent Application No. PCT/CA2015/050939. Once the positional data is in the coordinate system of the structured light system the left and right camera perspective transforms 420 and 425 can be used to project the tracked instrument 3D position into 2D representations 480 and 485 within the left and right camera 2D image space. The transformed left and right camera 2D positional data 480 and 485 can then be directly overlaid onto the rectified and undistorted video feed data 510 and 515 from the left and right cameras respectively. Referring once again to common implementations found in openCV, the rectification steps 500 and 505 can accomplished by calling the remap( ) function with inputs 430 and 435. The composite images 520 and 525 can then be displayed to the user to help orient untracked instruments.

Figure 7:
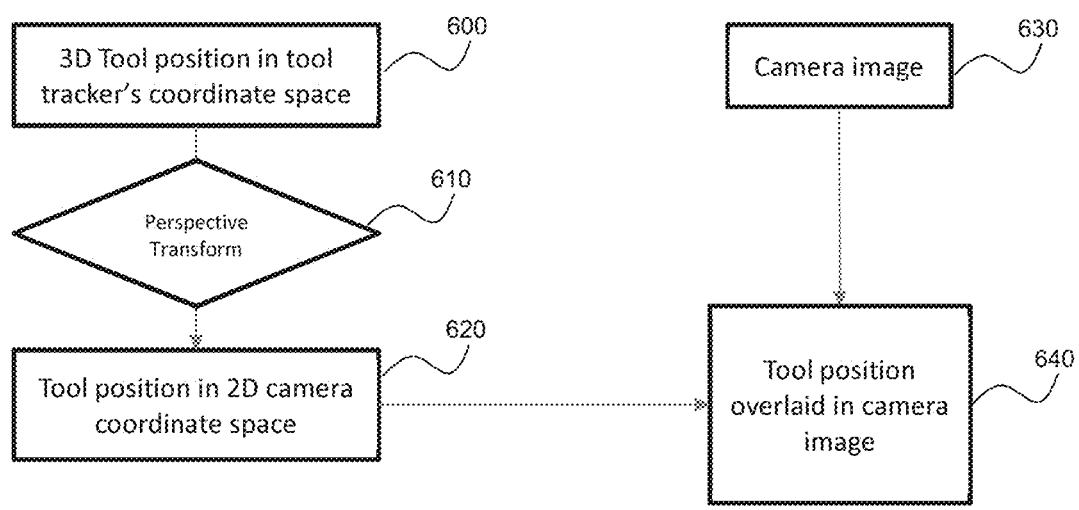
FIG. 7 is a flow chart illustrating an example process of generating and augmenting a video feed from a single camera.

The single camera embodiment shown in FIG. 7 utilizes a tracking system made up of one or more cameras/sensors to track the position of a medical instrument. The tracking system outputs the positional information 600 of tracked instruments. The tracking system is calibrated to the camera which outputs a 2D images 630 of the surgical field such that a known 3D position in the tracking system coordinate space can projected into the 2D camera image space. This transform 610 can be generally described as a perspective transform for mapping a 3D tool position to coordinates 620 in the 2D camera image space. It can be determined by using a set of known correspondences between points in the tracking systems 3D space and the corresponding points in the 2D image space. Once the positional information has been projected into the 2D image space it can be overlayed or rendered directly into a 2D image frame 640 for display to the user.

Figure 8:
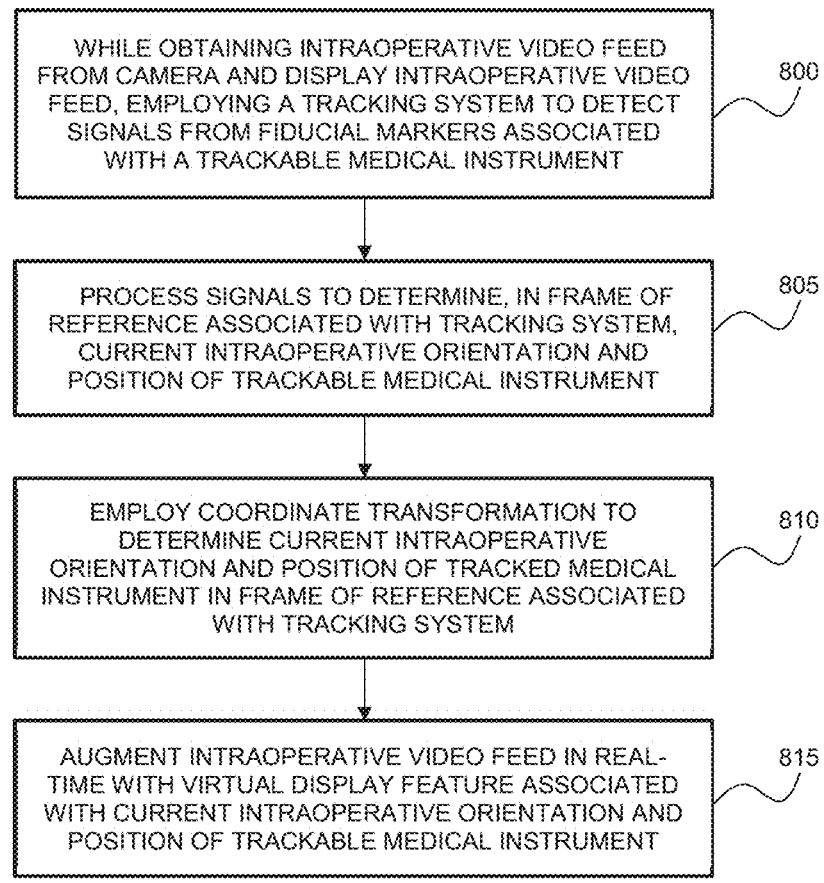
FIG. 8 is a flow chart illustrating an example method of providing intraoperative guidance, in which an intraoperative video feed is augmented in real time with a virtual display feature associated with the current intraoperative orientation and position of a trackable medical instrument.

Referring now to FIG. 8, a flow chart is provided that illustrates an alternative example method of augmenting an intraoperative video feed based on the intraoperative detection of the orientation and position of a trackable medical instrument. Unlike the aforementioned method involving the augmentation of an intraoperative video feed with a virtual display element associated with a previously determined intraoperative position and orientation of a tracked medical probe, the present example implementation involves the real-time augmentation of an intraoperative video feed with a virtual display element associated with the current (e.g. present or real-time) orientation and position of the tracked medical instrument. The virtual display element may therefore be dynamically displayed such that it is seen to move in the intraoperative video feed with a fixed spatial relationship relative to the tracked medical instrument.

In step 800, while a camera is employed to generate an intraoperative video feed, which is then intraoperatively displayed (e.g. on a display window of a navigation user interface), a tracking system is employed to detect signals from fiducial markers associated with a trackable medical instrument. The camera is configured such that a coordinate transformation is known between the frame of reference of the camera and the frame of reference of the tracking system. The signals are processed in step 805 to determine, in a frame of reference associated with the tracking system, an intraoperative orientation and position of the trackable medical instrument, for example, as described above with reference to FIG. 2.

In step 810, the current intraoperative orientation and position of the trackable medical instrument, as determined in step 805, is transformed into the frame of reference of the tracking system, using the known coordinate transformation between the frame of reference of the camera and the frame of reference of the tracking system. Having transformed the current intraoperative orientation and position of the trackable medical instrument into the frame of reference of the tracking system, the intraoperative video feed may be augmented with a virtual display feature that is associated with the current intraoperative orientation and position of the trackable medical instrument, as shown in 815.

For example, in one example embodiment, the intraoperative video feed may be augmented (e.g. annotated), at a prescribed spatial location or offset relative to the tracked medical probe, a virtual display element representing a tool or implant that is to be used in association with the tracked medical instrument during a medical procedure. The virtual display element may this be dynamically displayed in the intraoperative video feed with or at a fixed spatial relationship relative to the tracked medical instrument. In one example implementation, in which the virtual display element is an implant (or implantable device), the trackable medical instrument may include an elongate shaft having a longitudinal axis, and the virtual display of the surgical implant may be displayed along the longitudinal axis in a distal direction relative to a distal end of the elongate shaft.

Although the examples provided herein refer to medical instruments employed for performing spinal procedures, it will be understood that the methods and systems described herein are broadly applicable to a wide variety of medical procedures that a wide variety of trackable and untrackable medical instruments. For example, the methods and systems described herein may be employed for use in navigated medical procedures such as, but not limited to, medical procedures involving biopsy, deep brain stimulation electrode placement, robotic surgery, multi electrode placement for epilepsy, and laser interstitial therapy. Examples of tracked medical instruments include, but are not limited to probes, suction, drill, tap, screw driver, electro cautery, endoscope, laparoscope, pedicle finder, needles, and examples of untrackable medical instruments include, but are not limited to, taps, screw drivers, k-wires, forceps, scissors, scalpel, clamp, retractor, curette, speculum, needle driver, speculum, punches, and rongeurs.

Figure 9A:
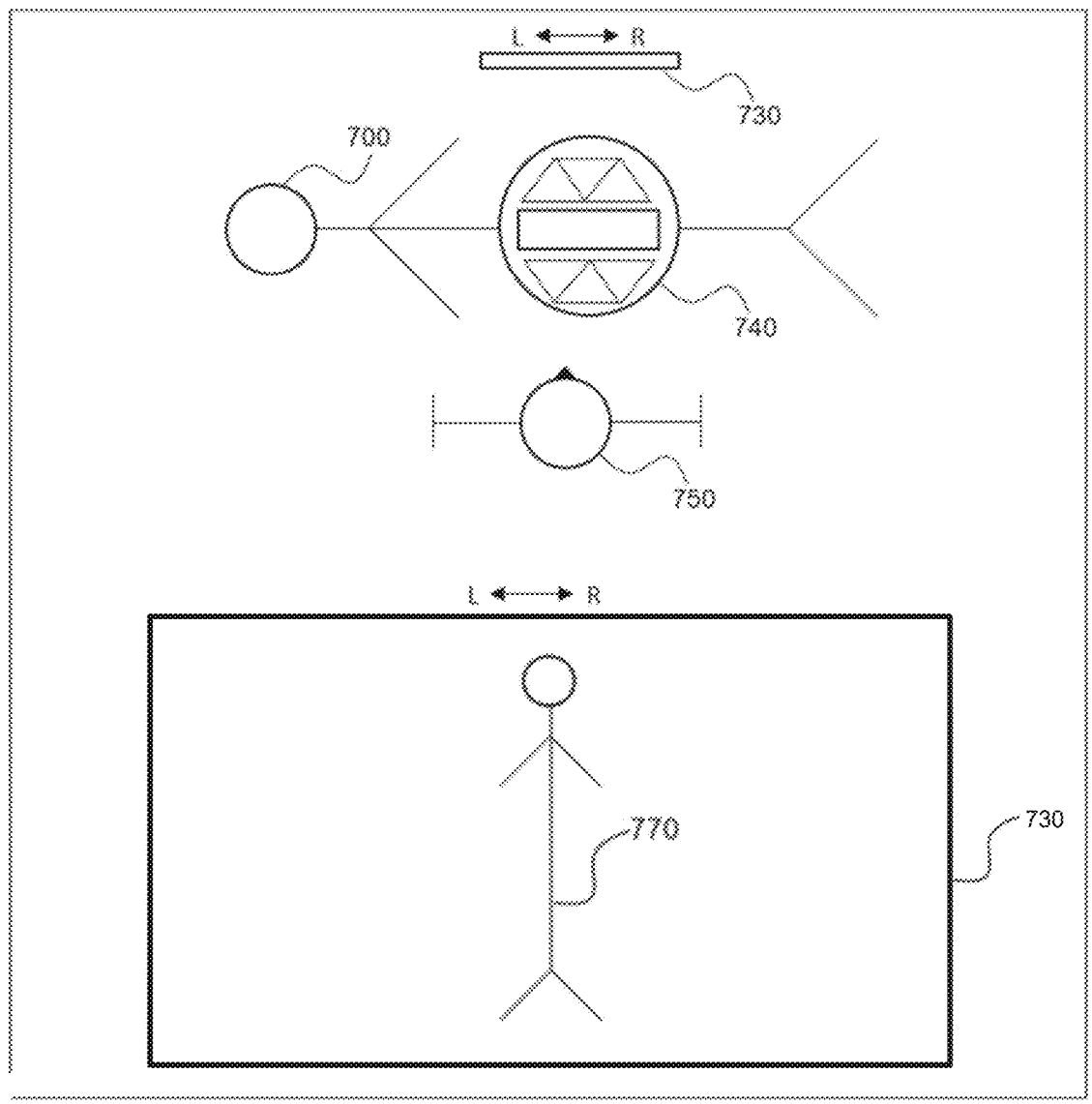
FIGS. 9A-9D show example embodiments in which a displayed video feed can be optionally rotated such that real-world motion is displayed in the correct orientation in the video feed.

Referring now to FIG. 9A, an overhead view of an operating room is shown, where a surgeon 750 is shown standing on the left side of the patient 700 who is positioned in a prone position. The navigation camera system 740 is positioned above the patient 700. The navigation view screen 730 is positioned on the right side of the patient with the screen facing the surgeon. During augmented reality display, the video feed of the patient 770 is shown oriented with the patient in a vertical orientation, with the result that horizontal hand motions of the surgeon 750 are displayed in vertical directions on the view screen 730. Such a configuration can be confusing and frustrating for the surgeon.

Figure 9B:
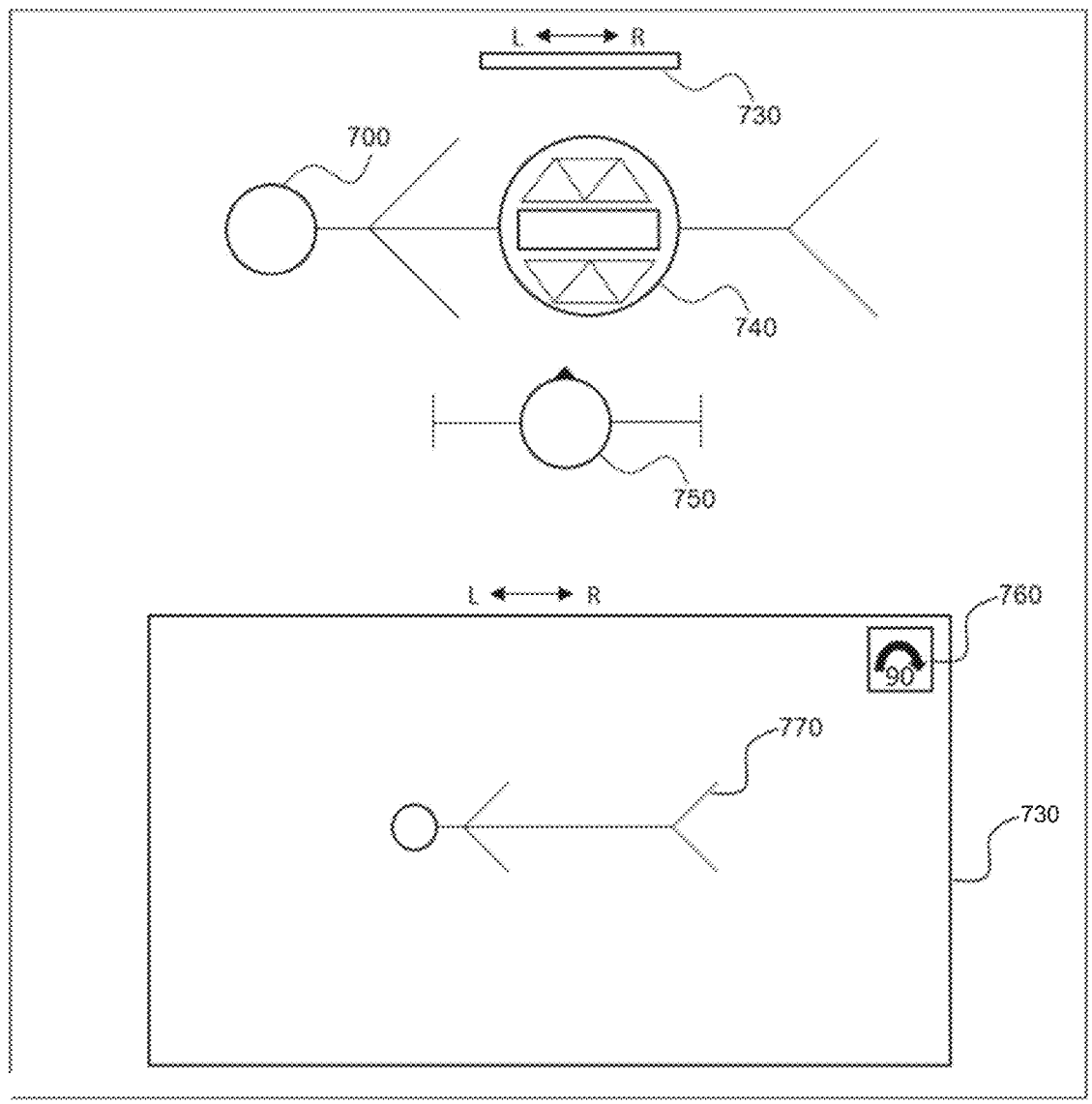

In order to correctly render surgeon motion, the user interface may be configured to facilitate the optional rotation of the displayed video feed. For example, as shown in FIG. 9B, the user interface may include a button 760 that can be selected to produce rotation of the displayed video feed. In various example implementations, the video feed may be continuously rotated or rotated by fixed rotation increments, such as 45, 90 or 180 degrees, in response to user input, in order to align the patient orientation seen in the video feed to that of the orientation of the patient in the operating room.

Figure 9C:
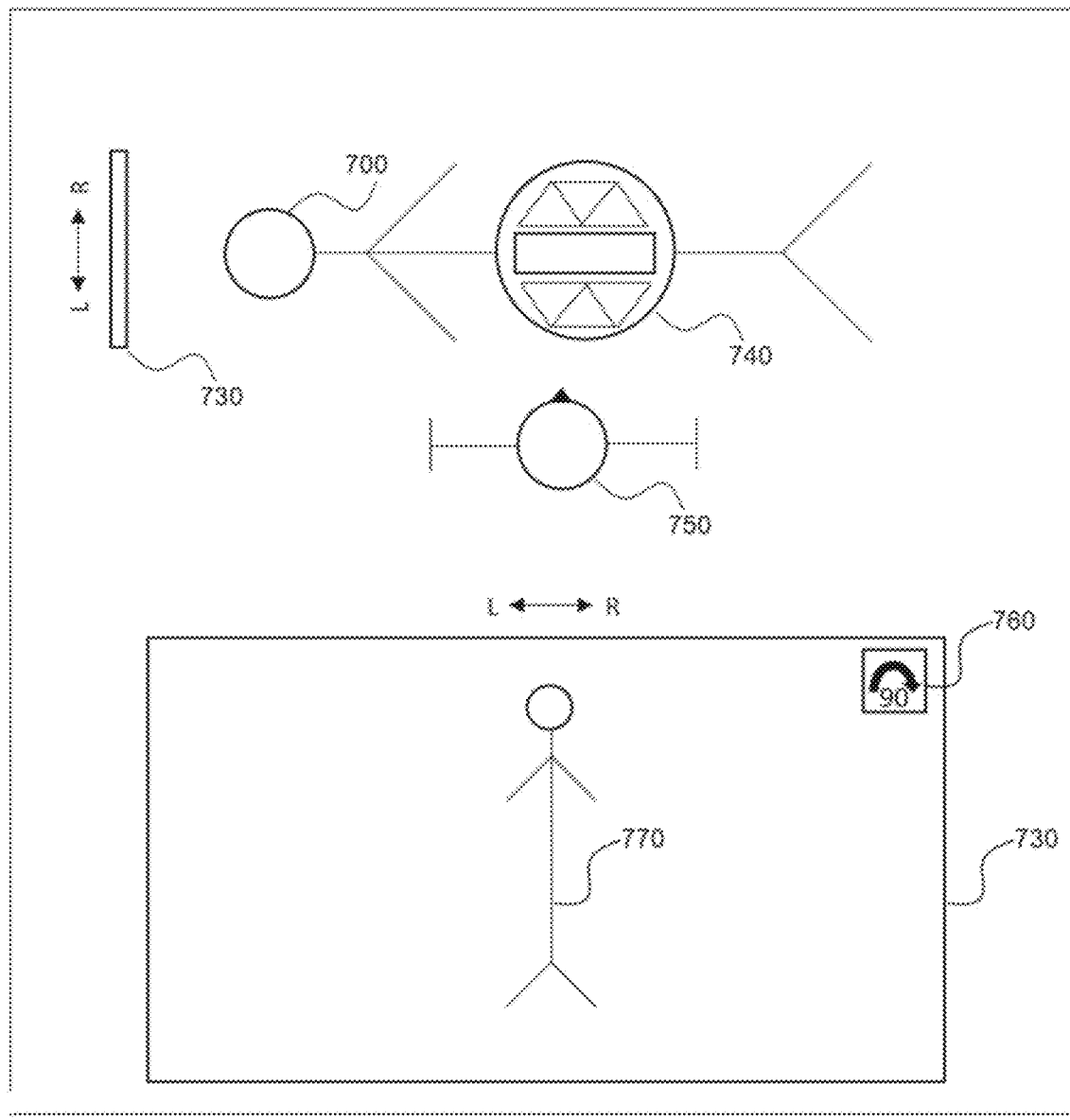

FIG. 9C illustrates an example in which the navigation view screen 730 is positioned near the head of the patient. During augmented reality display, the video feed 770 of the patient may be rotated such that the patient is vertically aligned, thereby aligning the real-world motions of of the surgeon with the motions displayed on the video feed. In the example implementation shown, the video feed can be rotated (for example, via a user interface button 760) by 90 degrees in order to align the patient orientation seen in the video feed to that of the orientation of the patient in the operating room.

Figure 9D:
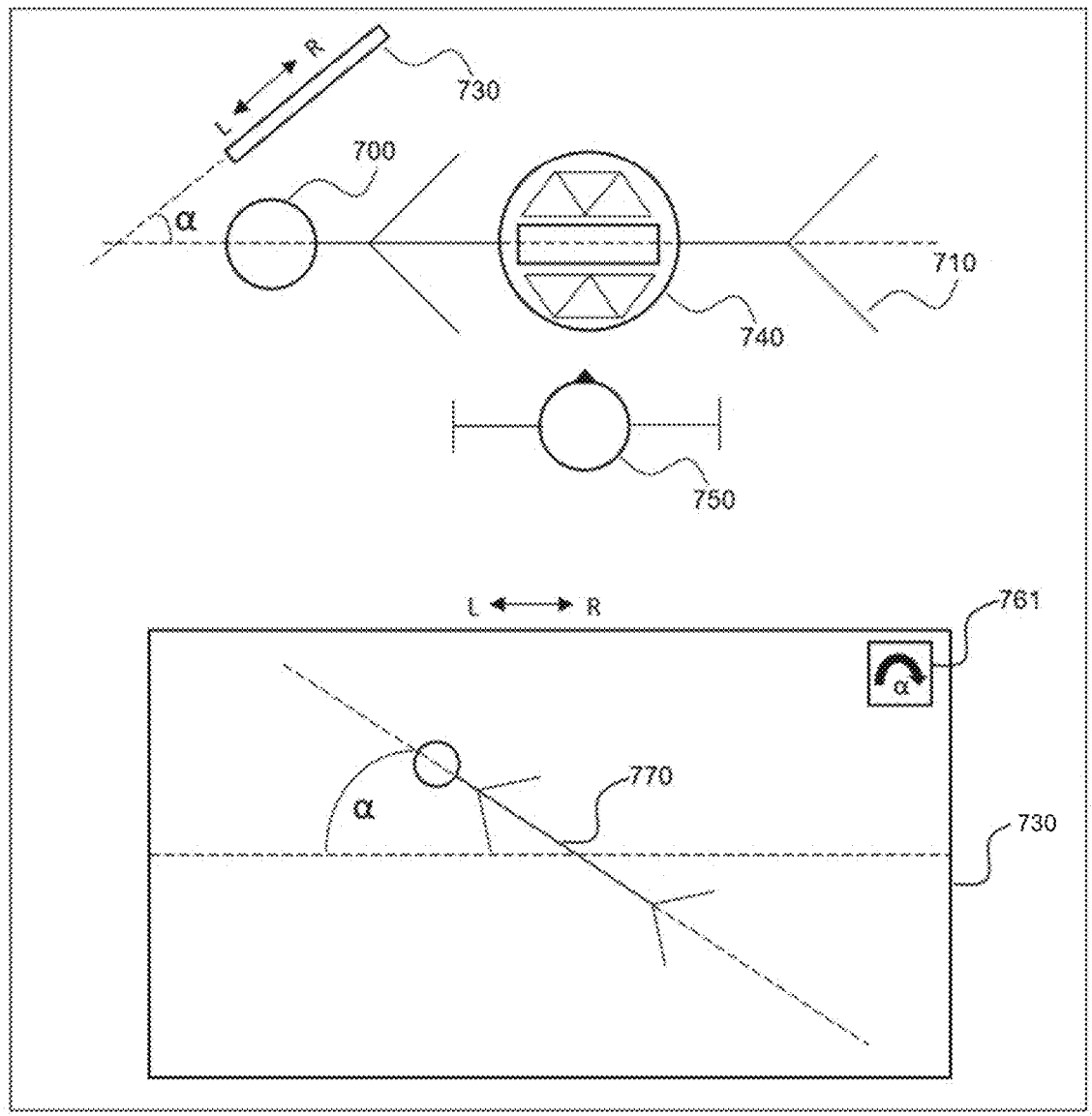

FIG. 9D depicts another example configuration in which the navigation view screen 730 is positioned at an oblique angle α relative to the superior-inferior axis of the patient. During augmented reality display, the video feed of the patient 770 can be rotated (e.g. via a user interface button 761) by a degrees in order to align the patient orientation seen in the video feed to that of the orientation of the patient in the operating room.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of aligning an untracked medical instrument, the method comprising:
  employing a tracking system to detect signals from fiducial markers associated with a trackable medical instrument;

processing the signals to determine, in a frame of reference associated with the tracking system, an intraoperative orientation and position of the trackable medical instrument;
employing a plurality of cameras to generate respective intraoperative video feeds involving different perspectives due to differences in camera alignment;
displaying the intraoperative video feeds;
for each camera, employing a respective coordinate transformation between a frame of reference associated with the camera and the frame of reference associated with the tracking system to augment the intraoperative video feed associated with the camera, such that the intraoperative video feed associated with the camera comprises a respective virtual display feature identifying the intraoperative orientation and position of the trackable medical instrument, thereby displaying a plurality of augmented intraoperative video feeds; and
employing the virtual display features within the plurality of augmented intraoperative video feeds to align the untracked medical instrument relative to the intraoperative orientation and position of the trackable medical instrument, wherein the untracked medical instrument not tracked by the tracking system.

2. The method according to claim 1 wherein the tracking system comprises a first camera and a second camera defining a stereo camera pair, the method further comprising: in the event that an accuracy of achieving visual alignment of the untracked medical instrument relative to the intraoperative orientation and position of the trackable medical instrument based on the virtual display feature is deemed to be impaired due to an alignment degeneracy, providing an indication to an operator, the indication instructing the operator to move and/or rotate the tracking system.

3. The method according to claim 1 wherein at least one intraoperative video feed is augmented such that the virtual display feature comprises a virtual display of the untracked medical instrument.

4. The method according to claim 1 wherein at least one intraoperative video feed is augmented such that the virtual display feature comprises a virtual display of a surgical implant.

5. The method according to claim 1 further comprising:
determining, based on the intraoperative orientation and position of the trackable medical instrument, a distal location corresponding to a distal end of the trackable medical instrument; and
within at least one intraoperative video feed, rendering the virtual display feature such that at least a portion of the virtual display feature is indicative of the distal location.

6. The method according to claim 1 wherein the intraoperative orientation and position is determined at a time at which input is received from an operator.

7. The method according to claim 1 wherein the intraoperative video feeds are augmented with the virtual display features when the trackable medical instrument is absent from a field of view of the tracking system.

8. The method according to claim 1 wherein further comprising processing the intraoperative orientation and position of the trackable medical instrument to determine an intraoperative axis based on a model of the trackable medical instrument.

9. The method according to claim 8 wherein the tracking system comprises a first camera and a second camera defining a stereo camera pair, the method further comprising:
determining whether or not the intraoperative axis lies within a plane that includes directional axes respectively associated with the first camera and the second camera; and
in the event that the intraoperative axis lies within a plane that includes directional axes respectively associated with the first camera and the second camera, providing an indication to an operator instructing the operator to move and/or rotate the tracking system to remove a degeneracy in determining the intraoperative axis.

10. The method according to claim 1 wherein the plurality of cameras are components of a surface detection system, and wherein the coordinate transformation is obtained according to a calibration between the surface detection system and the tracking system.

11. The method according to claim 10 further comprising:
employing an additional camera to obtain and display an additional intraoperative video feed, wherein the additional camera comprises additional fiducial markers, and wherein a position and orientation of the additional camera is tracked by the tracking system; and
employing an additional coordinate transformation between a frame of reference associated with the additional camera and the frame of reference associated with the tracking system to augment the additional intraoperative video feed with an additional virtual display feature associated with the intraoperative orientation and position of the trackable medical instrument.

12. The method according to claim 1 wherein the plurality of cameras comprise additional fiducial markers, and wherein a position and orientation of the plurality of cameras are tracked by the tracking system.

13. The method according to claim 12 wherein the plurality of cameras are movable, thereby permitting viewing of the intraoperative video feeds annotated with the virtual display feature from multiple viewing directions.

14. The method according to claim 1 wherein the tracking system is rigidly fixed relative to the plurality of cameras.

15. A system for providing intraoperative guidance for aligning an untracked medical instrument, the system comprising:
a tracking subsystem;
a display;
a plurality of cameras configured to generate intraoperative video feeds involving different perspectives due to differences in camera alignment; and
computer hardware operatively coupled to said tracking subsystem and said plurality of cameras, wherein said computer hardware comprises memory coupled with one or more processors to store instructions, which when executed by the one or more processors, causes the one or more processors to perform operations comprising:
employing said tracking subsystem to detect signals from fiducial markers associated with a trackable medical instrument that is trackable by said tracking subsystem;
processing the signals to determine, in a frame of reference associated with said tracking subsystem, an intraoperative orientation and position of the trackable medical instrument;

employing said plurality of cameras to obtain the intraoperative video feeds;

displaying the intraoperative video feeds on the display; and for each camera, employing a respective coordinate transformation between a frame of reference associated with the camera and the frame of reference associated with said tracking subsystem to augment the intraoperative video feed associated with the camera, such that the intraoperative video feed associated with the camera comprises a respective virtual display feature identifying the previously determined intraoperative orientation and position of the trackable medical instrument, thereby providing multi-directional perspectives that enable visual alignment of an untracked medical instrument that is not tracked by said tracking subsystem, relative to the intraoperative orientation and position of the trackable medical instrument.

16. The system according to claim 15 wherein said tracking subsystem comprises a first camera and a second camera defining a stereo camera pair, wherein said computer hardware is configured to perform operations further comprising:

employing the intraoperative orientation and position of the trackable medical instrument, relative to the first camera and the second camera, to determine that an accuracy of achieving visual alignment of the untracked medical instrument relative to the intraoperative orientation and position of the trackable medical instrument, based on the virtual display feature, is deemed to be impaired due to an alignment degeneracy; and providing an indication to an operator, the indication instructing the operator to move and/or rotate said tracking subsystem.

17. The system according to claim 15 wherein said computer hardware is configured such that at least one intraoperative video feed is augmented such that the virtual display feature comprises a virtual display of the untracked medical instrument.

18. The system according to claim 15 wherein said computer hardware is configured such that at least one intraoperative video feed is augmented such that the virtual display feature comprises a virtual display of a surgical implant.

19. The system according to claim 15 wherein said computer hardware is configured to perform operations further comprising:

determining, based on the intraoperative orientation and position of the trackable medical instrument, a distal location corresponding to a distal end of the trackable medical instrument; and within at least one intraoperative video feed, rendering the virtual display feature such that at least a portion of the virtual display feature is indicative of the distal location.

20. The system according to claim 15 wherein said computer hardware is configured such that the intraoperative orientation and position is determined in response to input received from an operator.

* * * * *